United States Patent
Van Kampen et al.

(10) Patent No.: US 11,780,894 B2
(45) Date of Patent: Oct. 10, 2023

(54) HORNFLY VACCINE METHODS

(71) Applicant: TNG Pharmaceuticals, Inc., Louisville, KY (US)

(72) Inventors: Kent R. Van Kampen, Payson, UT (US); Serge Martinod, Groton, CT (US)

(73) Assignee: TNG Pharmaceuticals, Inc., Louisville, KY (US)

( * ) Notice: Subject to any disclaimer, the term of this patent is extended or adjusted under 35 U.S.C. 154(b) by 464 days.

(21) Appl. No.: 16/771,800

(22) PCT Filed: Dec. 13, 2018

(86) PCT No.: PCT/US2018/065407
§ 371 (c)(1),
(2) Date: Jun. 11, 2020

(87) PCT Pub. No.: WO2019/118696
PCT Pub. Date: Jun. 20, 2019

(65) Prior Publication Data
US 2021/0070818 A1    Mar. 11, 2021

Related U.S. Application Data

(60) Provisional application No. 62/598,658, filed on Dec. 14, 2017.

(51) Int. Cl.
*C07K 14/435* (2006.01)
*A61K 39/00* (2006.01)

(52) U.S. Cl.
CPC .... *C07K 14/43577* (2013.01); *A61K 39/0003* (2013.01); *A61K 2039/552* (2013.01); *A61K 2039/575* (2013.01); *C07K 2319/24* (2013.01); *C07K 2319/40* (2013.01)

(58) Field of Classification Search
None
See application file for complete search history.

(56) References Cited

U.S. PATENT DOCUMENTS

2012/0263742 A1*  10/2012  Cupp ................ A61K 39/0003
424/185.1

FOREIGN PATENT DOCUMENTS

WO    WO 2000/011172 A1    3/2000

OTHER PUBLICATIONS

Chiarella, Pieranna, et al. "Antigenic features of protein carriers commonly used in immunisation trials." *Biotechnology letters* 32.9 (2010): 1215-1221.
Cupp, Mary S., et al. "Evaluation of a recombinant salivary gland protein (thrombostasin) as a vaccine candidate to disrupt blood-feeding by horn flies." *Vaccine* 22.17-18 (2004): 2285-2297.
Cupp, MS, EW Cupp, C Navarre, D Zhang, X Yue, L Todd, V Panangala. 2010. Salivary gland thrombostasin isoforms differentially regulate blood uptake of horn flies fed on control- and thrombostasin-vaccinated cattle. J. Med. Entomol. 47(4):610-617.
Cupp, Mary. Vaccination of Cattle with Recombinant Salivary Proteins of Horn Flies (*Haematobia irritans irritans*). 000 0000: 20th International Conference of the World Association for the Advancement of Veterinary Parasitology (WAAVP 2005) (0000000). Christchurch (New Zealand). Oct. 16-20, 2005. World Association for the Advancement of Veterinary Parasitology (WAAVP). [Abstract Only].
Di Guana, Chu, et al. "Vectors that facilitate the expression and purification of foreign peptides in *Escherichia coli* by fusion to maltose-binding protein." *Gene* 67.1 (1988): 21-30.
International Search Report and Written Opinion dated Feb. 25, 2019 for International Application No. PCT/US2018/065407, 12 pages.

* cited by examiner

*Primary Examiner* — Shanon A. Foley
(74) *Attorney, Agent, or Firm* — FROST BROWN TODD LLP

(57) ABSTRACT

Disclosed herein are fusion proteins comprising a truncated thrombostasin protein having at least 85% sequence homology to a thrombostasin protein, wherein the thrombostasin protein has a carboxy terminal deletion; and a fusion partner protein that is a non-thrombostasin protein. Further disclosed are vaccine compositions thrombostasin proteins having a comprising a carboxy terminal deletion, and methods for inhibiting a response to a thrombostasin protein in a host in need thereof, comprising the disclosed fusion proteins or vaccine compositions. Further disclosed are methods for the preparation of a fusion protein composition.

12 Claims, 3 Drawing Sheets

Specification includes a Sequence Listing.

Protocol 2a
Raw ELISA DATA Truncated Thrombostasin Recombinant Antigen

| Group | A | A | A | A | B | B | B | B | C | C | C |
|---|---|---|---|---|---|---|---|---|---|---|---|
| Day 0 | 758 | 763 | 767 | 768 | 760 | 762 | 765 | 766 | 759 | 761 | 764 |
| TB8N5 | 0 | 0.086 | 0 | 0.044 | 0 | 0 | 0.066 | 0 | 0 | 0.005 | 0.127 |
| TS9N5 | 0 | 0.171 | 0 | 0.019 | 0 | 0 | 0.031 | 0 | 0 | 0.058 | 0.102 |
| TS10N5 | 0 | 0.109 | 0 | 0.089 | 0 | 0 | 0.061 | 0 | 0 | 0.003 | 0.149 |
| TB5 | 0.129 | 0.053 | 0 | 0.12 | 0 | 0 | 0.106 | 0 | 2.492 | 0.084 | 0.189 |
| TS8 | 0.152 | 0.026 | 0 | 0.155 | 0 | 0 | 0.089 | 0 | 0 | 0.201 | 0.145 |
| TS9 | 1.255 | 0.037 | 0 | 0.244 | 0 | 0 | 0.085 | 0 | 0 | 0.058 | 0.137 |
| TS10 | 0.284 | 0.103 | 0 | 0.349 | 0 | 0 | 0.117 | 0 | 0.07 | 0.081 | 0.19 |
| | | | | | | | | | | | |
| Day 21 | 758 | 763 | 767 | 768 | 760 | 762 | 765 | 766 | 759 | 761 | 764 |
| TB8N5 | 1.481 | 1.45 | 0.998 | 1.164 | 0.756 | 0.266 | 0.632 | 0.809 | 0.042 | 0.016 | 0.022 |
| TS9N5 | 1.585 | 1.571 | 1.162 | 1.219 | 0.808 | 0.216 | 0.879 | 0.7 | 0.031 | 0.005 | 0.01 |
| TS10N5 | 1.703 | 1.686 | 1.164 | 1.129 | 0.904 | 0.293 | 0.926 | 0.812 | 0.048 | 0 | 0.042 |
| TB5 | 2.787 | 2.515 | 2.065 | 0.867 | 1.268 | 1.34 | 1.462 | 1.456 | 0.031 | 0.041 | 0.013 |
| TS8 | 2.213 | 2.723 | 2.221 | 1.353 | 1.358 | 1.625 | 1.727 | 1.552 | 0.044 | 0.072 | 0.024 |
| TS9 | 2.461 | 2.699 | 2.319 | 1.193 | 1.241 | 1.608 | 1.67 | 1.462 | 0.045 | 0.057 | 0.022 |
| TS10 | 2.477 | 2.515 | 2.21 | 1.16 | 1.25 | 1.635 | 1.477 | 1.428 | 0.064 | 0.11 | 0.036 |
| | | | | | | | | | | | |
| Day 35 | 758 | 763 | 767 | 768 | 760 | 762 | 765 | 766 | 759 | 761 | 764 |
| TB8N5 | 0.229 | 1.763 | 1.219 | 1.465 | 2.6 | 1.773 | 2.272 | 2.701 | 0.202 | 0.135 | 0.186 |
| TS9N5 | 0.224 | 1.986 | 1.369 | 1.544 | 2.833 | 1.963 | 2.47 | 2.602 | 0.195 | 0.161 | 0.193 |
| TS10N5 | 0.282 | 2.042 | 1.442 | 1.918 | 3.041 | 2.061 | 2.629 | 2.848 | 0.194 | 0.173 | 0.199 |
| TB5 | 0.356 | 3.215 | 2.783 | 2.609 | 3.509 | 3.469 | 3.509 | 3.509 | 0.23 | 0.151 | 0.213 |
| TS8 | 0.333 | 3.268 | 2.799 | 2.55 | 3.509 | 3.444 | 3.509 | 3.509 | 0.253 | 0.145 | 0.229 |
| TS9 | 0.354 | 3.444 | 2.876 | 2.541 | 3.509 | 3.509 | 3.509 | 3.509 | 0.225 | 0.152 | 0.222 |
| TS10 | 0.386 | 3.387 | 2.759 | 2.573 | 3.509 | 3.509 | 3.509 | 3.509 | 0.239 | 0.194 | 0.308 |

FIG. 3

SEQUENCE LISTING

```
<160> NUMBER OF SEQ ID NOS: 24

<210> SEQ ID NO 1
<211> LENGTH: 157
<212> TYPE: PRT
<213> ORGANISM: Haematobia irritans

<400> SEQUENCE: 1

Gln Asn Val Leu Ser Gly Arg Arg Gln His Gly Ala Gln Gly Leu Ser
1               5                   10                  15

Gly Tyr Ser Gly Asp Asn Asp Trp Gly Tyr Tyr Gly Glu Ala Gly Ala
            20                  25                  30

Pro Gly Ser Asp Tyr Ser Gly Ser Ser Gly Gln Trp Ala Pro Leu Asp
        35                  40                  45

Phe Asp Tyr Asn Ser Leu Pro Gly Leu Ser Gly Tyr Asn His Glu Gln
    50                  55                  60

Gln Asp Tyr Glu Glu Asp Ser Tyr Arg His Val Arg Ser Ala Gly Pro
65                  70                  75                  80

Ile Thr Leu Gln Leu Asp Asp Asp Asp Asp Asp Ser Gly Ile Pro
                85                  90                  95

Ile Phe Glu Met Asp Asp Glu Asp Glu Asp Ser Asn Asp Asn Gln Lys
                100                 105                 110

Phe Pro Leu Ser Phe Glu Arg Phe Pro Glu Asn Glu Lys Asn Gln Glu
            115                 120                 125

Gly Leu Arg Ala Arg Phe Asn Lys Phe Met Ala Lys Phe Thr Ser Leu
        130                 135                 140

Phe Gly Arg Arg Arg Gly Val Asp Val Pro Asn Ala Ala
145                 150                 155

<210> SEQ ID NO 2
<211> LENGTH: 157
<212> TYPE: PRT
<213> ORGANISM: Haematobia irritans

<400> SEQUENCE: 2

Gln Asn Val Leu Ser Gly Arg Arg Gln His Gly Ala Gln Gly Leu Ser
1               5                   10                  15

Gly Tyr Ser Gly Asp Asn Asp Trp Gly Tyr Tyr Gly Glu Ala Gly Ala
            20                  25                  30

Pro Gly Ser Asp Tyr Ser Gly Ser Ser Gly Gln Trp Ala Pro Leu Asp
        35                  40                  45

Phe Asp Tyr Asn Ser Leu Pro Gly Leu Ser Gly Tyr Asn His Glu Gln
    50                  55                  60

Gln Asp Tyr Glu Glu Asp Ser Tyr Arg His Val Arg Ser Ala Gly Pro
65                  70                  75                  80

Ile Thr Leu Gln Leu Asp Asp Asp Asp Asp Asp Ser Gly Ile Pro
                85                  90                  95

Ile Phe Glu Met Asp Asp Glu Asp Glu Asp Ser Asn Asp Asn Gln Lys
                100                 105                 110

Phe Pro Leu Ser Phe Glu Arg Phe Pro Glu Asn Glu Lys Asn Gln Val
            115                 120                 125
```

```
Gly Leu Arg Ala Arg Phe Asn Lys Phe Met Ala Lys Phe Thr Ser Leu
        130                 135                 140

Phe Gly Arg Arg Arg Gly Val Asn Val Pro Asn Ala Ala
145                 150                 155
```

<210> SEQ ID NO 3
<211> LENGTH: 157
<212> TYPE: PRT
<213> ORGANISM: Haematobia irritans

<400> SEQUENCE: 3

```
Gln Asn Leu Val Ser Gly Arg Arg Gln His Gly Ala Gln Gly Leu Ser
1               5                   10                  15

Gly Tyr Ser Gly Asp Asn Asp Trp Gly Tyr Tyr Gly Glu Ala Gly Ala
            20                  25                  30

Pro Gly Ser Asp Tyr Ser Gly Ser Gly Gln Trp Ala Pro Leu Asp
            35                  40                  45

Phe Asp Tyr Asn Ser Leu Pro Gly Leu Ser Gly Tyr Asn His Glu Gln
50                  55                  60

Gln Asp Tyr Glu Glu Asp Ser Tyr Arg His Val Arg Ser Ala Gly Pro
65                  70                  75                  80

Ile Thr Leu Gln Leu Asp Asp Asp Asp Asp Ser Gly Ile Pro
            85                  90                  95

Ile Phe Glu Met Asp Asp Glu Asp Val Asp Ser Asn Asp Asn Gln Lys
            100                 105                 110

Phe Pro Leu Ser Phe Glu Arg Phe Pro Glu Asn Glu Lys Asn Gln Val
        115                 120                 125

Gly Leu Arg Ala Arg Phe Asn Lys Phe Met Ala Lys Phe Thr Ser Leu
        130                 135                 140

Phe Gly Arg Arg Arg Gly Val Asn Val Pro Asn Ala Ala
145                 150                 155
```

<210> SEQ ID NO 4
<211> LENGTH: 157
<212> TYPE: PRT
<213> ORGANISM: Haematobia irritans

<400> SEQUENCE: 4

```
Gln Asn Val Leu Ser Gly Arg Arg Gln His Gly Ala Gln Gly Leu Ser
1               5                   10                  15

Gly Tyr Ser Gly Asp Asn Asp Trp Gly Tyr Tyr Gly Glu Ala Gly Ala
            20                  25                  30

Pro Gly Ser Asp Tyr Ser Gly Ser Gly Gln Trp Ala Pro Leu Asp
            35                  40                  45

Phe Asp Tyr Asn Ser Leu Pro Gly Leu Ser Gly Tyr Asn His Glu Gln
50                  55                  60

Gln Asp Tyr Glu Glu Asp Ser Tyr Arg His Val Arg Ser Ala Gly Pro
65                  70                  75                  80

Ile Thr Leu Gln Leu Asp Asp Asp Asp Asp Ser Gly Ile Pro
            85                  90                  95

Ile Phe Glu Met Asp Asp Glu Asp Val Asp Ser Asn Asp Asn Gln Lys
            100                 105                 110

Phe Pro Leu Ser Phe Glu Arg Phe Pro Glu Asn Glu Lys Asn Gln Glu
        115                 120                 125

Gly Leu Arg Ala Arg Phe Asn Lys Phe Met Ala Lys Phe Thr Ser Leu
        130                 135                 140
```

Phe Gly Arg Arg Arg Ser Val Asp Val Pro Asn Ala Ala
145                 150                 155

<210> SEQ ID NO 5
<211> LENGTH: 157
<212> TYPE: PRT
<213> ORGANISM: Haematobia irritans

<400> SEQUENCE: 5

Gln Asn Val Leu Ser Gly Arg Arg Gln His Gly Ala Gln Gly Leu Ser
1               5                   10                  15

Gly Tyr Ser Gly Asp Asn Asp Trp Gly Tyr Tyr Gly Glu Ala Gly Ala
            20                  25                  30

Pro Gly Ser Asp Tyr Ser Gly Ser Gly Gln Trp Ala Pro Leu Asp
            35                  40                  45

Phe Asp Tyr Asn Ser Leu Pro Gly Leu Ser Gly Tyr Asn His Glu Gln
50                  55                  60

Gln Asp Tyr Glu Glu Asp Ser Tyr Arg His Val Arg Ser Ala Gly Pro
65                  70                  75                  80

Ile Thr Leu Gln Leu Asn Asp Asp Asp Asp Ser Gly Ile Pro
                85                  90                  95

Ile Phe Glu Met Asp Asp Glu Asp Glu Asp Ser Asn Asp Asn Gln Lys
                100                 105                 110

Phe Pro Leu Ser Phe Glu Arg Phe Pro Glu Asn Glu Lys Asn Gln Glu
            115                 120                 125

Gly Leu Arg Ala Arg Phe Asn Lys Phe Met Ala Lys Phe Thr Ser Leu
        130                 135                 140

Phe Gly Arg Arg Arg Gly Val Asp Val Pro Asn Ala Ala
145                 150                 155

<210> SEQ ID NO 6
<211> LENGTH: 157
<212> TYPE: PRT
<213> ORGANISM: Haematobia irritans

<400> SEQUENCE: 6

Gln Asn Val Leu Ser Gly Arg Arg Gln His Gly Ala Gln Gly Leu Ser
1               5                   10                  15

Gly Tyr Ser Gly Asp Asn Asp Trp Gly Tyr Tyr Gly Glu Ala Gly Ala
            20                  25                  30

Pro Gly Ser Asp Tyr Ser Gly Ser Gly Gln Trp Ala Pro Leu Asp
            35                  40                  45

Phe Asp Tyr Asn Ser Leu Pro Gly Leu Ser Gly Tyr Asn His Glu Gln
50                  55                  60

Gln Asp Tyr Glu Glu Asp Ser Tyr Arg His Val Arg Ser Ala Gly Pro
65                  70                  75                  80

Ile Thr Leu Gln Leu Asp Asp Asp Asp Asp Ser Gly Ile Pro
                85                  90                  95

Ile Phe Glu Met Asp Asp Glu Asp Glu Asp Ser Asn Asp Asn Gln Lys
                100                 105                 110

Phe Pro Leu Ser Phe Glu Arg Phe Pro Glu Asn Glu Lys Asn Gln Val
            115                 120                 125

Gly Leu Arg Ala Arg Phe Asn Lys Phe Met Ala Lys Phe Thr Ser Leu
        130                 135                 140

Phe Gly Arg Arg Arg Gly Val Asp Val Pro Asn Ala Ala
145                 150                 155

<210> SEQ ID NO 7
<211> LENGTH: 157
<212> TYPE: PRT
<213> ORGANISM: Haematobia irritans

<400> SEQUENCE: 7

```
Gln Asn Val Leu Ser Gly Arg Arg Gln His Gly Ala Gln Gly Leu Ser
1               5                   10                  15

Gly Tyr Ser Gly Asp Asn Asp Trp Gly Tyr Tyr Gly Glu Ala Gly Ala
            20                  25                  30

Pro Gly Ser Asp Tyr Ser Gly Ser Gly Gln Trp Ala Pro Leu Asp
        35                  40                  45

Phe Asp Tyr Asn Ser Leu Pro Gly Leu Ser Gly Tyr Asn His Glu Gln
50                  55                  60

Gln Asp Tyr Glu Glu Asp Ser Tyr Arg His Val Arg Ser Ala Gly Pro
65                  70                  75                  80

Ile Thr Leu Gln Leu Asp Asp Asp Asp Asp Asp Ser Gly Ile Pro
                85                  90                  95

Ile Phe Glu Met Asp Asp Glu Asp Glu Asp Ser Asn Asp Asn Gln Lys
                100                 105                 110

Phe Pro Leu Ser Phe Glu Arg Phe Pro Glu Asn Glu Lys Asn Gln Glu
            115                 120                 125

Gly Leu Arg Ala Arg Phe Asn Lys Phe Met Ala Lys Phe Thr Ser Leu
        130                 135                 140

Phe Gly Arg Arg Arg Gly Val Asn Val Pro Asn Ala Ala
145                 150                 155
```

<210> SEQ ID NO 8
<211> LENGTH: 157
<212> TYPE: PRT
<213> ORGANISM: Haematobia irritans

<400> SEQUENCE: 8

```
Gln Asn Val Leu Ser Gly Arg Arg Gln His Gly Ala Gln Gly Leu Ser
1               5                   10                  15

Gly Tyr Ser Gly Asp Asn Asp Trp Gly Tyr Tyr Gly Glu Ala Gly Ala
            20                  25                  30

Pro Gly Ser Asp Tyr Ser Gly Ser Gly Gln Trp Ala Pro Leu Asp
        35                  40                  45

Phe Asp Tyr Asn Ser Leu Pro Gly Leu Ser Gly Tyr Asn His Glu Gln
50                  55                  60

Gln Asp Tyr Glu Glu Asp Ser Tyr Arg His Val Arg Ser Ala Gly Pro
65                  70                  75                  80

Ile Thr Leu Gln Leu Asp Asp Asp Asp Asp Asp Ser Gly Ile Pro
                85                  90                  95

Ile Phe Glu Met Asp Asp Glu Asp Glu Asp Ser Asn Asp Asn Gln Lys
                100                 105                 110

Phe Pro Leu Ser Phe Glu Arg Phe Pro Glu Asn Glu Lys Asn Gln Glu
            115                 120                 125

Gly Leu Arg Ala Arg Phe Asn Lys Phe Met Ala Lys Phe Thr Ser Leu
        130                 135                 140

Phe Gly Arg Arg Arg Ser Val Asn Val Pro Asn Ala Ala
145                 150                 155
```

<210> SEQ ID NO 9
<211> LENGTH: 157

<212> TYPE: PRT
<213> ORGANISM: Haematobia irritans

<400> SEQUENCE: 9

Gln Asn Val Leu Ser Gly Arg Arg Gln His Gly Ala Gln Gly Leu Ser
1               5                   10                  15

Gly Tyr Ser Gly Asp Asn Asp Trp Gly Tyr Tyr Gly Glu Ala Gly Ala
            20                  25                  30

Pro Gly Ser Asp Tyr Ser Gly Ser Gly Gln Trp Ala Pro Leu Asp
        35                  40                  45

Phe Asp Tyr Asn Ser Leu Pro Gly Leu Ser Gly Tyr Asn His Glu Gln
    50                  55                  60

Gln Asp Tyr Glu Glu Asp Ser Tyr Arg His Val Arg Ser Ala Gly Pro
65                  70                  75                  80

Ile Thr Leu Gln Leu Asp Asp Asp Asp Asp Ser Gly Ile Pro
                85                  90                  95

Ile Phe Glu Met Asp Asp Glu Asp Glu Asp Ser Asn Asp Asn Gln Lys
                    100                 105                 110

Phe Pro Leu Ser Phe Glu Arg Phe Pro Glu Asn Glu Lys Asn Gln Val
                115                 120                 125

Gly Leu Arg Ala Arg Phe Asn Lys Phe Met Ala Lys Phe Thr Ser Leu
            130                 135                 140

Phe Gly Arg Arg Arg Gly Val Asp Val Pro Asn Ala Ala
145                 150                 155

<210> SEQ ID NO 10
<211> LENGTH: 157
<212> TYPE: PRT
<213> ORGANISM: Haematobia irritans

<400> SEQUENCE: 10

Gln Asn Val Leu Ser Gly Arg Arg Gln His Gly Ala Gln Gly Leu Ser
1               5                   10                  15

Gly Tyr Ser Gly Asp Asn Asp Trp Gly Tyr Tyr Gly Glu Ala Gly Ala
            20                  25                  30

Pro Gly Ser Asp Tyr Ser Gly Ser Gly Gln Trp Ala Pro Leu Asp
        35                  40                  45

Phe Asp Tyr Asn Ser Leu Pro Gly Leu Ser Gly Tyr Asn His Glu Gln
    50                  55                  60

Gln Asp Tyr Glu Glu Asp Ser Tyr Arg His Val Arg Ser Ala Gly Pro
65                  70                  75                  80

Ile Thr Leu Gln Leu Asp Asp Asp Asp Asp Ser Gly Ile Pro
                85                  90                  95

Ile Phe Glu Met Asp Asp Glu Asp Glu Asp Ser Asn Asp Asn Gln Lys
                    100                 105                 110

Phe Pro Leu Ser Phe Glu Arg Phe Pro Glu Asn Glu Lys Asn Gln Gln
                115                 120                 125

Gly Leu Arg Ala Arg Phe Asn Lys Phe Met Ala Lys Phe Thr Ser Leu
            130                 135                 140

Phe Gly Arg Arg Arg Gly Val Asp Val Pro Asn Ala Ala
145                 150                 155

<210> SEQ ID NO 11
<211> LENGTH: 157
<212> TYPE: PRT
<213> ORGANISM: Haematobia irritans

<400> SEQUENCE: 11

Gln Asn Val Leu Ser Gly Arg Arg Gln His Gly Ala Gln Gly Leu Ser
1               5                   10                  15

Gly Tyr Ser Gly Asp Asn Asp Trp Gly Tyr Tyr Gly Glu Ala Gly Ala
                20                  25                  30

Pro Gly Ser Asp Tyr Ser Gly Ser Gly Gln Trp Ala Pro Leu Asp
            35                  40                  45

Phe Asp Tyr Asn Ser Leu Pro Gly Leu Ser Gly Tyr Asn His Glu Gln
        50                  55                  60

Gln Asp Tyr Glu Glu Asp Ser Tyr Arg His Val Arg Ser Ala Gly Pro
65                  70                  75                  80

Ile Thr Leu Gln Leu Asp Asp Asp Asp Asp Ser Gly Ile Pro
                85                  90                  95

Ile Phe Glu Met Asp Asp Glu Asp Glu Asp Ser Asn Asp Asn Gln Lys
                100                 105                 110

Phe Pro Leu Ser Phe Glu Arg Phe Pro Glu Asn Glu Lys Asn Gln Leu
            115                 120                 125

Gly Leu Arg Ala Arg Phe Asn Lys Phe Met Ala Lys Phe Thr Ser Leu
        130                 135                 140

Phe Gly Arg Arg Arg Gly Val Asp Val Pro Asn Ala Ala
145                 150                 155

<210> SEQ ID NO 12
<211> LENGTH: 157
<212> TYPE: PRT
<213> ORGANISM: Haematobia irritans

<400> SEQUENCE: 12

Gln Asn Val Leu Ser Gly Arg Arg Gln His Gly Ala Gln Gly Leu Ser
1               5                   10                  15

Gly Tyr Ser Gly Asp Asn Asp Trp Gly Tyr Tyr Gly Glu Ala Gly Ala
                20                  25                  30

Pro Gly Ser Asp Tyr Ser Gly Ser Gly Gln Trp Ala Pro Leu Asp
            35                  40                  45

Phe Asp Tyr Asn Ser Leu Pro Gly Leu Ser Gly Tyr Asn His Glu Gln
        50                  55                  60

Gln Asp Tyr Glu Glu Asp Ser Tyr Arg His Val Arg Ser Ala Gly Pro
65                  70                  75                  80

Ile Thr Leu Gln Leu Asp Asp Asp Asp Asp Ser Gly Ile Pro
                85                  90                  95

Ile Phe Glu Met Asp Asp Glu Asp Glu Asp Ser Asn Asp Asn Gln Lys
                100                 105                 110

Phe Pro Leu Ser Phe Glu Arg Phe Pro Glu Asn Glu Lys Asn Gln Val
            115                 120                 125

Gly Leu Arg Ala Arg Phe Asn Lys Phe Met Ala Lys Phe Thr Ser Leu
        130                 135                 140

Phe Gly Arg Arg Arg Ser Val Asn Val Pro Asn Ala Ala
145                 150                 155

<210> SEQ ID NO 13
<211> LENGTH: 135
<212> TYPE: PRT
<213> ORGANISM: Haematobia irritans

<400> SEQUENCE: 13

Gln Asn Leu Val Ser Gly Arg Arg Gln His Gly Ala Gln Gly Leu Ser

```
1               5                   10                  15
Gly Tyr Ser Gly Asp Asn Asp Trp Gly Tyr Tyr Gly Glu Ala Gly Ala
            20                  25                  30

Pro Gly Ser Asp Tyr Ser Gly Ser Ser Gly Gln Trp Ala Pro Leu Asp
            35                  40                  45

Phe Asp Tyr Asn Ser Leu Pro Gly Leu Ser Gly Tyr Asn His Glu Gln
    50                  55                  60

Gln Asp Tyr Glu Glu Asp Ser Tyr Arg His Val Arg Ser Ala Gly Pro
65                  70                  75                  80

Ile Thr Leu Gln Leu Asp Asp Asp Asp Asp Asp Ser Gly Ile Pro
            85                  90                  95

Ile Phe Glu Met Asp Asp Glu Asp Val Asp Ser Asn Asp Asn Gln Lys
            100                 105                 110

Phe Pro Leu Ser Phe Glu Arg Phe Pro Glu Asn Glu Lys Asn Gln Val
            115                 120                 125

Gly His His His His His
    130                 135
```

```
<210> SEQ ID NO 14
<211> LENGTH: 135
<212> TYPE: PRT
<213> ORGANISM: Haematobia irritans

<400> SEQUENCE: 14

Gln Asn Val Leu Ser Gly Arg Arg Gln His Gly Ala Gln Gly Leu Ser
1               5                   10                  15

Gly Tyr Ser Gly Asp Asn Asp Trp Gly Tyr Tyr Gly Glu Ala Gly Ala
            20                  25                  30

Pro Gly Ser Asp Tyr Ser Gly Ser Ser Gly Gln Trp Ala Pro Leu Asp
            35                  40                  45

Phe Asp Tyr Asn Ser Leu Pro Gly Leu Ser Gly Tyr Asn His Glu Gln
    50                  55                  60

Gln Asp Tyr Glu Glu Asp Ser Tyr Arg His Val Arg Ser Ala Gly Pro
65                  70                  75                  80

Ile Thr Leu Gln Leu Asp Asp Asp Asp Asp Asp Ser Gly Ile Pro
            85                  90                  95

Ile Phe Glu Met Asp Asp Glu Asp Val Asp Ser Asn Asp Asn Gln Lys
            100                 105                 110

Phe Pro Leu Ser Phe Glu Arg Phe Pro Glu Asn Glu Lys Asn Gln Glu
            115                 120                 125

Gly His His His His His
    130                 135
```

```
<210> SEQ ID NO 15
<211> LENGTH: 135
<212> TYPE: PRT
<213> ORGANISM: Haematobia irritans

<400> SEQUENCE: 15

Gln Asn Val Leu Ser Gly Arg Arg Gln His Gly Ala Gln Gly Leu Ser
1               5                   10                  15

Gly Tyr Ser Gly Asp Asn Asp Trp Gly Tyr Tyr Gly Glu Ala Gly Ala
            20                  25                  30

Pro Gly Ser Asp Tyr Ser Gly Ser Ser Gly Gln Trp Ala Pro Leu Asp
            35                  40                  45

Phe Asp Tyr Asn Ser Leu Pro Gly Leu Ser Gly Tyr Asn His Glu Gln
```

```
                    50                  55                  60
Gln Asp Tyr Glu Glu Asp Ser Tyr Arg His Val Arg Ser Ala Gly Pro
 65                  70                  75                  80

Ile Thr Leu Gln Leu Asp Asp Asp Asp Asp Ser Gly Ile Pro
                 85                  90                  95

Ile Phe Glu Met Asp Asp Glu Asp Glu Asp Ser Asn Asp Asn Gln Lys
                100                 105                 110

Phe Pro Leu Ser Phe Glu Arg Phe Pro Glu Asn Glu Lys Asn Gln Val
                115                 120                 125

Gly His His His His His
                130                 135

<210> SEQ ID NO 16
<211> LENGTH: 556
<212> TYPE: PRT
<213> ORGANISM: Artificial Sequence
<220> FEATURE:
<223> OTHER INFORMATION: MBP-TS9 (Fusion Protein - MBP + TS9)

<400> SEQUENCE: 16

Met Lys Ile Glu Glu Gly Lys Leu Val Ile Trp Ile Asn Gly Asp Lys
 1               5                  10                  15

Gly Tyr Asn Gly Leu Ala Glu Val Gly Lys Lys Phe Glu Lys Asp Thr
                 20                  25                  30

Gly Ile Lys Val Thr Val Glu His Pro Asp Lys Leu Glu Glu Lys Phe
                 35                  40                  45

Pro Gln Val Ala Ala Thr Gly Asp Gly Pro Asp Ile Ile Phe Trp Ala
 50                  55                  60

His Asp Arg Phe Gly Gly Tyr Ala Gln Ser Gly Leu Leu Ala Glu Ile
 65                  70                  75                  80

Thr Pro Asp Lys Ala Phe Gln Asp Lys Leu Tyr Pro Phe Thr Trp Asp
                 85                  90                  95

Ala Val Arg Tyr Asn Gly Lys Leu Ile Ala Tyr Pro Ile Ala Val Glu
                100                 105                 110

Ala Leu Ser Leu Ile Tyr Asn Lys Asp Leu Leu Pro Asn Pro Pro Lys
                115                 120                 125

Thr Trp Glu Glu Ile Pro Ala Leu Asp Lys Glu Leu Lys Ala Lys Gly
                130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
                180                 185                 190

Leu Thr Phe Leu Val Asp Leu Ile Lys Asn Lys His Met Asn Ala Asp
                195                 200                 205

Thr Asp Tyr Ser Ile Ala Glu Ala Ala Phe Asn Lys Gly Glu Thr Ala
                210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
                260                 265                 270

Asn Lys Glu Leu Ala Lys Glu Phe Leu Glu Asn Tyr Leu Leu Thr Asp
```

```
                    275                 280                 285
Glu Gly Leu Glu Ala Val Asn Lys Asp Lys Pro Leu Gly Ala Val Ala
    290                 295                 300

Leu Lys Ser Tyr Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
            340                 345                 350

Ser Gly Arg Gln Thr Val Asp Glu Ala Leu Lys Asp Ala Gln Thr Asn
        355                 360                 365

Ser Ser Ser Asn Asn Asn Asn Asn Asn Asn Asn Asn Leu Gly Ile
    370                 375                 380

Glu Gly Arg Ile Ser Glu Phe Gly Ser Gln Asn Val Leu Ser Gly Arg
385                 390                 395                 400

Arg Gln His Gly Ala Gln Gly Leu Ser Gly Tyr Ser Gly Asp Asn Asp
                405                 410                 415

Trp Gly Tyr Tyr Gly Glu Ala Gly Ala Pro Gly Ser Asp Tyr Ser Gly
            420                 425                 430

Ser Ser Gly Gln Trp Ala Pro Leu Asp Phe Asp Tyr Asn Ser Leu Pro
        435                 440                 445

Gly Leu Ser Gly Tyr Asn His Glu Gln Gln Asp Tyr Glu Glu Asp Ser
    450                 455                 460

Tyr Arg His Val Arg Ser Ala Gly Pro Ile Thr Leu Gln Leu Asp Asp
465                 470                 475                 480

Asp Asp Asp Asp Asp Ser Gly Ile Pro Ile Phe Glu Met Asp Asp Glu
                485                 490                 495

Asp Glu Asp Ser Asn Asp Asn Gln Lys Phe Pro Leu Ser Phe Glu Arg
            500                 505                 510

Phe Pro Glu Asn Glu Lys Asn Gln Glu Gly Leu Arg Ala Arg Phe Asn
        515                 520                 525

Lys Phe Met Ala Lys Phe Thr Ser Leu Phe Gly Arg Arg Gly Val
    530                 535                 540

Asp Val Pro Asn Ala Ala His His His His His
545                 550                 555

<210> SEQ ID NO 17
<211> LENGTH: 304
<212> TYPE: PRT
<213> ORGANISM: Artificial Sequence
<220> FEATURE:
<223> OTHER INFORMATION: PAF-TS9 (Fusion Protein - PAF + TS9) Protein

<400> SEQUENCE: 17

Met Lys Leu Thr Ile Glu Ser Thr Pro Phe Asn Val Ala Glu Gly Lys
1               5                   10                  15

Glu Val Leu Leu Leu Val His Asn Leu Pro Gln His Leu Phe Gly Tyr
            20                  25                  30

Ser Trp Tyr Lys Gly Glu Arg Val Asp Gly Asn Arg Gln Ile Ile Gly
        35                  40                  45

Tyr Val Ile Gly Thr Gln Gln Ala Thr Pro Gly Pro Ala Tyr Ser Gly
    50                  55                  60

Arg Glu Ile Ile Tyr Pro Asn Ala Ser Leu Leu Ile Gln Asn Ile Ile
65                  70                  75                  80

Gln Asn Asp Thr Gly Phe Tyr Thr Leu His Val Ile Lys Ser Asp Leu
```

```
                    85                  90                  95
Val Asn Glu Glu Ala Thr Gly Gln Phe Arg Val Tyr Pro Glu Leu Pro
                100                 105                 110

Lys Pro Ser Ile Ser Ser Asn Asn Ser Lys Pro Val Glu Asp Lys Asp
            115                 120                 125

Ala Val Ala Phe Thr Cys Glu Pro Glu Thr Gln Asp Ala Gln Asn Val
        130                 135                 140

Leu Ser Gly Arg Arg Gln His Gly Ala Gln Gly Leu Ser Gly Tyr Ser
145                 150                 155                 160

Gly Asp Asn Asp Trp Gly Tyr Tyr Gly Glu Ala Gly Ala Pro Gly Ser
                165                 170                 175

Asp Tyr Ser Gly Ser Ser Gly Gln Trp Ala Pro Leu Asp Phe Asp Tyr
                180                 185                 190

Asn Ser Leu Pro Gly Leu Ser Gly Tyr Asn His Glu Gln Gln Asp Tyr
            195                 200                 205

Glu Glu Asp Ser Tyr Arg His Val Arg Ser Ala Gly Pro Ile Thr Leu
        210                 215                 220

Gln Leu Asp Asp Asp Asp Asp Asp Ser Gly Ile Pro Ile Phe Glu
225                 230                 235                 240

Met Asp Asp Glu Asp Glu Asp Ser Asn Asp Asn Gln Lys Phe Pro Leu
                245                 250                 255

Ser Phe Glu Arg Phe Pro Glu Asn Glu Lys Asn Gln Glu Gly Leu Arg
            260                 265                 270

Ala Arg Phe Asn Lys Phe Met Ala Lys Phe Thr Ser Leu Phe Gly Arg
        275                 280                 285

Arg Arg Gly Val Asp Val Pro Asn Ala Ala His His His His His His
    290                 295                 300

<210> SEQ ID NO 18
<211> LENGTH: 276
<212> TYPE: PRT
<213> ORGANISM: Artificial Sequence
<220> FEATURE:
<223> OTHER INFORMATION: PAF-TS9N5 (Fusion Protein - PAF + Truncated
      TS9) Protein

<400> SEQUENCE: 18

Met Lys Leu Thr Ile Glu Ser Thr Pro Phe Asn Val Ala Gly Lys
1               5                   10                  15

Glu Val Leu Leu Leu Val His Asn Leu Pro Gln His Leu Phe Gly Tyr
            20                  25                  30

Ser Trp Tyr Lys Gly Glu Arg Val Asp Gly Asn Arg Gln Ile Ile Gly
        35                  40                  45

Tyr Val Ile Gly Thr Gln Gln Ala Thr Pro Gly Pro Ala Tyr Ser Gly
    50                  55                  60

Arg Glu Ile Ile Tyr Pro Asn Ala Ser Leu Leu Ile Gln Asn Ile Ile
65                  70                  75                  80

Gln Asn Asp Thr Gly Phe Tyr Thr Leu His Val Ile Lys Ser Asp Leu
                85                  90                  95

Val Asn Glu Glu Ala Thr Gly Gln Phe Arg Val Tyr Pro Glu Leu Pro
                100                 105                 110

Lys Pro Ser Ile Ser Ser Asn Asn Ser Lys Pro Val Glu Asp Lys Asp
            115                 120                 125

Ala Val Ala Phe Thr Cys Glu Pro Glu Thr Gln Asp Ala Gln Asn Val
        130                 135                 140
```

```
Leu Ser Gly Arg Arg Gln His Gly Ala Gln Gly Leu Ser Gly Tyr Ser
145                 150                 155                 160

Gly Asp Asn Asp Trp Gly Tyr Tyr Gly Glu Ala Gly Ala Pro Gly Ser
                165                 170                 175

Asp Tyr Ser Gly Ser Ser Gly Gln Trp Ala Pro Leu Asp Phe Asp Tyr
            180                 185                 190

Asn Ser Leu Pro Gly Leu Ser Gly Tyr Asn His Glu Gln Gln Asp Tyr
        195                 200                 205

Glu Glu Asp Ser Tyr Arg His Val Arg Ser Ala Gly Pro Ile Thr Leu
    210                 215                 220

Gln Leu Asp Asp Asp Asp Asp Ser Gly Ile Pro Ile Phe Glu
225                 230                 235                 240

Met Asp Asp Glu Asp Glu Asp Ser Asn Asp Asn Gln Lys Phe Pro Leu
                245                 250                 255

Ser Phe Glu Arg Phe Pro Glu Asn Glu Lys Asn Gln Glu Gly His His
            260                 265                 270

His His His His
        275

<210> SEQ ID NO 19
<211> LENGTH: 304
<212> TYPE: PRT
<213> ORGANISM: Artificial Sequence
<220> FEATURE:
<223> OTHER INFORMATION: PAF-TB8 (Fusion Protein - PAF + TB8) Protein

<400> SEQUENCE: 19

Met Lys Leu Thr Ile Glu Ser Thr Pro Phe Asn Val Ala Glu Gly Lys
1               5                   10                  15

Glu Val Leu Leu Leu Val His Asn Leu Pro Gln His Leu Phe Gly Tyr
            20                  25                  30

Ser Trp Tyr Lys Gly Glu Arg Val Asp Gly Asn Arg Gln Ile Ile Gly
        35                  40                  45

Tyr Val Ile Gly Thr Gln Gln Ala Thr Pro Gly Pro Ala Tyr Ser Gly
    50                  55                  60

Arg Glu Ile Ile Tyr Pro Asn Ala Ser Leu Leu Ile Gln Asn Ile Ile
65                  70                  75                  80

Gln Asn Asp Thr Gly Phe Tyr Thr Leu His Val Ile Lys Ser Asp Leu
                85                  90                  95

Val Asn Glu Glu Ala Thr Gly Gln Phe Arg Val Tyr Pro Glu Leu Pro
            100                 105                 110

Lys Pro Ser Ile Ser Ser Asn Asn Ser Lys Pro Val Glu Asp Lys Asp
        115                 120                 125

Ala Val Ala Phe Thr Cys Glu Pro Glu Thr Gln Asp Ala Gln Asn Leu
    130                 135                 140

Val Ser Gly Arg Arg Gln His Gly Ala Gln Gly Leu Ser Gly Tyr Ser
145                 150                 155                 160

Gly Asp Asn Asp Trp Gly Tyr Tyr Gly Glu Ala Gly Ala Pro Gly Ser
                165                 170                 175

Asp Tyr Ser Gly Ser Ser Gly Gln Trp Ala Pro Leu Asp Phe Asp Tyr
            180                 185                 190

Asn Ser Leu Pro Gly Leu Ser Gly Tyr Asn His Glu Gln Gln Asp Tyr
        195                 200                 205

Glu Glu Asp Ser Tyr Arg His Val Arg Ser Ala Gly Pro Ile Thr Leu
    210                 215                 220
```

```
Gln Leu Asp Asp Asp Asp Asp Asp Ser Gly Ile Pro Ile Phe Glu
225                 230                 235                 240

Met Asp Asp Glu Asp Val Asp Ser Asn Asp Asn Gln Lys Phe Pro Leu
            245                 250                 255

Ser Phe Glu Arg Phe Pro Glu Asn Glu Lys Asn Gln Val Gly Leu Arg
                260                 265                 270

Ala Arg Phe Asn Lys Phe Met Ala Lys Phe Thr Ser Leu Phe Gly Arg
            275                 280                 285

Arg Arg Gly Val Asn Val Pro Asn Ala Ala His His His His His His
        290                 295                 300
```

<210> SEQ ID NO 20
<211> LENGTH: 276
<212> TYPE: PRT
<213> ORGANISM: Artificial Sequence
<220> FEATURE:
<223> OTHER INFORMATION: PAF-TB8N5 (Fusion Protein - PAF + Truncated TB8) Protein

<400> SEQUENCE: 20

```
Met Lys Leu Thr Ile Glu Ser Thr Pro Phe Asn Val Ala Glu Gly Lys
1               5                   10                  15

Glu Val Leu Leu Leu Val His Asn Leu Pro Gln His Leu Phe Gly Tyr
                20                  25                  30

Ser Trp Tyr Lys Gly Glu Arg Val Asp Gly Asn Arg Gln Ile Ile Gly
            35                  40                  45

Tyr Val Ile Gly Thr Gln Gln Ala Thr Pro Gly Pro Ala Tyr Ser Gly
        50                  55                  60

Arg Glu Ile Ile Tyr Pro Asn Ala Ser Leu Leu Ile Gln Asn Ile Ile
65                  70                  75                  80

Gln Asn Asp Thr Gly Phe Tyr Thr Leu His Val Ile Lys Ser Asp Leu
                85                  90                  95

Val Asn Glu Glu Ala Thr Gly Gln Phe Arg Val Tyr Pro Glu Leu Pro
            100                 105                 110

Lys Pro Ser Ile Ser Ser Asn Asn Ser Lys Pro Val Glu Asp Lys Asp
        115                 120                 125

Ala Val Ala Phe Thr Cys Glu Pro Glu Thr Gln Asp Ala Gln Asn Leu
130                 135                 140

Val Ser Gly Arg Arg Gln His Gly Ala Gln Gly Leu Ser Gly Tyr Ser
145                 150                 155                 160

Gly Asp Asn Asp Trp Gly Tyr Tyr Gly Glu Ala Gly Ala Pro Gly Ser
                165                 170                 175

Asp Tyr Ser Gly Ser Ser Gly Gln Trp Ala Pro Leu Asp Phe Asp Tyr
            180                 185                 190

Asn Ser Leu Pro Gly Leu Ser Gly Tyr Asn His Glu Gln Gln Asp Tyr
        195                 200                 205

Glu Glu Asp Ser Tyr Arg His Val Arg Ser Ala Gly Pro Ile Thr Leu
    210                 215                 220

Gln Leu Asp Asp Asp Asp Asp Asp Ser Gly Ile Pro Ile Phe Glu
225                 230                 235                 240

Met Asp Asp Glu Asp Val Asp Ser Asn Asp Asn Gln Lys Phe Pro Leu
            245                 250                 255

Ser Phe Glu Arg Phe Pro Glu Asn Glu Lys Asn Gln Val Gly His His
                260                 265                 270

His His His His
        275
```

<210> SEQ ID NO 21
<211> LENGTH: 528
<212> TYPE: PRT
<213> ORGANISM: Artificial Sequence
<220> FEATURE:
<223> OTHER INFORMATION: MBP-TS9N5 Protein

<400> SEQUENCE: 21

```
Met Lys Ile Glu Glu Gly Lys Leu Val Ile Trp Ile Asn Gly Asp Lys
1               5                   10                  15

Gly Tyr Asn Gly Leu Ala Glu Val Gly Lys Lys Phe Glu Lys Asp Thr
            20                  25                  30

Gly Ile Lys Val Thr Val Glu His Pro Asp Lys Leu Glu Glu Lys Phe
        35                  40                  45

Pro Gln Val Ala Ala Thr Gly Asp Gly Pro Asp Ile Ile Phe Trp Ala
    50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
    130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
        195                 200                 205

Thr Asp Tyr Ser Ile Ala Glu Ala Ala Phe Asn Lys Gly Glu Thr Ala
    210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
            260                 265                 270

Asn Lys Glu Leu Ala Lys Glu Phe Leu Glu Asn Tyr Leu Leu Thr Asp
        275                 280                 285

Glu Gly Leu Glu Ala Val Asn Lys Asp Lys Pro Leu Gly Ala Val Ala
    290                 295                 300

Leu Lys Ser Tyr Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
            340                 345                 350

Ser Gly Arg Gln Thr Val Asp Glu Ala Leu Lys Asp Ala Gln Thr Asn
        355                 360                 365
```

```
Ser Ser Ser Asn Asn Asn Asn Asn Asn Asn Asn Leu Gly Ile
    370             375                 380

Glu Gly Arg Ile Ser Glu Phe Gly Ser Gln Asn Val Leu Ser Gly Arg
385                 390                 395                 400

Arg Gln His Gly Ala Gln Gly Leu Ser Gly Tyr Ser Gly Asp Asn Asp
                405                 410                 415

Trp Gly Tyr Tyr Gly Glu Ala Gly Ala Pro Gly Ser Asp Tyr Ser Gly
                420                 425                 430

Ser Ser Gly Gln Trp Ala Pro Leu Asp Phe Asp Tyr Asn Ser Leu Pro
            435                 440                 445

Gly Leu Ser Gly Tyr Asn His Glu Gln Gln Asp Tyr Glu Glu Asp Ser
        450                 455                 460

Tyr Arg His Val Arg Ser Ala Gly Pro Ile Thr Leu Gln Leu Asp Asp
465                 470                 475                 480

Asp Asp Asp Asp Asp Ser Gly Ile Pro Ile Phe Glu Met Asp Asp Glu
                485                 490                 495

Asp Glu Asp Ser Asn Asp Asn Gln Lys Phe Pro Leu Ser Phe Glu Arg
                500                 505                 510

Phe Pro Glu Asn Glu Lys Asn Gln Glu Gly His His His His His His
            515                 520                 525
```

<210> SEQ ID NO 22
<211> LENGTH: 528
<212> TYPE: PRT
<213> ORGANISM: Artificial Sequence
<220> FEATURE:
<223> OTHER INFORMATION: MBP-TS10N5 Protein

<400> SEQUENCE: 22

```
Met Lys Ile Glu Glu Gly Lys Leu Val Ile Trp Ile Asn Gly Asp Lys
1               5                   10                  15

Gly Tyr Asn Gly Leu Ala Glu Val Gly Lys Lys Phe Glu Lys Asp Thr
            20                  25                  30

Gly Ile Lys Val Thr Val Glu His Pro Asp Lys Leu Glu Glu Lys Phe
        35                  40                  45

Pro Gln Val Ala Ala Thr Gly Asp Gly Pro Asp Ile Ile Phe Trp Ala
    50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
                100                 105                 110

Ala Leu Ser Leu Ile Tyr Asn Lys Asp Leu Leu Pro Asn Pro Pro Lys
            115                 120                 125

Thr Trp Glu Glu Ile Pro Ala Leu Asp Lys Glu Leu Lys Ala Lys Gly
        130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
                180                 185                 190

Leu Thr Phe Leu Val Asp Leu Ile Lys Asn Lys His Met Asn Ala Asp
            195                 200                 205
```

-continued

```
Thr Asp Tyr Ser Ile Ala Glu Ala Ala Phe Asn Lys Gly Glu Thr Ala
            210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
            260                 265                 270

Asn Lys Glu Leu Ala Lys Glu Phe Leu Glu Asn Tyr Leu Leu Thr Asp
        275                 280                 285

Glu Gly Leu Glu Ala Val Asn Lys Asp Lys Pro Leu Gly Ala Val Ala
290                 295                 300

Leu Lys Ser Tyr Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
            340                 345                 350

Ser Gly Arg Gln Thr Val Asp Glu Ala Leu Lys Asp Ala Gln Thr Asn
        355                 360                 365

Ser Ser Ser Asn Asn Asn Asn Asn Asn Asn Asn Asn Leu Gly Ile
370                 375                 380

Glu Gly Arg Ile Ser Glu Phe Gly Ser Gln Asn Val Leu Ser Gly Arg
385                 390                 395                 400

Arg Gln His Gly Ala Gln Gly Leu Ser Gly Tyr Ser Gly Asp Asn Asp
                405                 410                 415

Trp Gly Tyr Tyr Gly Glu Ala Gly Ala Pro Gly Ser Asp Tyr Ser Gly
            420                 425                 430

Ser Ser Gly Gln Trp Ala Pro Leu Asp Phe Asp Tyr Asn Ser Leu Pro
        435                 440                 445

Gly Leu Ser Gly Tyr Asn His Glu Gln Gln Asp Tyr Glu Glu Asp Ser
450                 455                 460

Tyr Arg His Val Arg Ser Ala Gly Pro Ile Thr Leu Gln Leu Asp Asp
465                 470                 475                 480

Asp Asp Asp Asp Asp Ser Gly Ile Pro Ile Phe Glu Met Asp Asp Glu
                485                 490                 495

Asp Glu Asp Ser Asn Asp Asn Gln Lys Phe Pro Leu Ser Phe Glu Arg
            500                 505                 510

Phe Pro Glu Asn Glu Lys Asn Gln Val Gly His His His His His
        515                 520                 525
```

```
<210> SEQ ID NO 23
<211> LENGTH: 528
<212> TYPE: PRT
<213> ORGANISM: Artificial Sequence
<220> FEATURE:
<223> OTHER INFORMATION: MBP-TB8N5 Protein

<400> SEQUENCE: 23
```

```
Met Lys Ile Glu Glu Gly Lys Leu Val Ile Trp Ile Asn Gly Asp Lys
1               5                   10                  15

Gly Tyr Asn Gly Leu Ala Glu Val Gly Lys Lys Phe Glu Lys Asp Thr
            20                  25                  30

Gly Ile Lys Val Thr Val Glu His Pro Asp Lys Leu Glu Glu Lys Phe
        35                  40                  45
```

-continued

```
Pro Gln Val Ala Ala Thr Gly Asp Gly Pro Asp Ile Ile Phe Trp Ala
     50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
    130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
        195                 200                 205

Thr Asp Tyr Ser Ile Ala Glu Ala Ala Phe Asn Lys Gly Glu Thr Ala
    210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
            260                 265                 270

Asn Lys Glu Leu Ala Lys Glu Phe Leu Glu Asn Tyr Leu Leu Thr Asp
        275                 280                 285

Glu Gly Leu Glu Ala Val Asn Lys Asp Lys Pro Leu Gly Ala Val Ala
    290                 295                 300

Leu Lys Ser Tyr Glu Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
            340                 345                 350

Ser Gly Arg Gln Thr Val Asp Glu Ala Leu Lys Asp Ala Gln Thr Asn
        355                 360                 365

Ser Ser Ser Asn Asn Asn Asn Asn Asn Asn Asn Asn Leu Gly Ile
    370                 375                 380

Glu Gly Arg Ile Ser Glu Phe Gly Ser Gln Asn Leu Val Ser Gly Arg
385                 390                 395                 400

Arg Gln His Gly Ala Gln Gly Leu Ser Gly Tyr Ser Gly Asp Asn Asp
                405                 410                 415

Trp Gly Tyr Tyr Gly Glu Ala Gly Ala Pro Gly Ser Asp Tyr Ser Gly
            420                 425                 430

Ser Ser Gly Gln Trp Ala Pro Leu Asp Phe Asp Tyr Asn Ser Leu Pro
        435                 440                 445

Gly Leu Ser Gly Tyr Asn His Glu Gln Gln Asp Tyr Glu Glu Asp Ser
    450                 455                 460
```

```
Tyr Arg His Val Arg Ser Ala Gly Pro Ile Thr Leu Gln Leu Asp Asp
465                 470                 475                 480

Asp Asp Asp Asp Asp Ser Gly Ile Pro Ile Phe Glu Met Asp Asp Glu
            485                 490                 495

Asp Val Asp Ser Asn Asp Asn Gln Lys Phe Pro Leu Ser Phe Glu Arg
                500                 505                 510

Phe Pro Glu Asn Glu Lys Asn Gln Val Gly His His His His His His
        515                 520                 525

<210> SEQ ID NO 24
<211> LENGTH: 30
<212> TYPE: PRT
<213> ORGANISM: Artificial Sequence
<220> FEATURE:
<223> OTHER INFORMATION: TS9 Deletion

<400> SEQUENCE: 24

Leu Arg Ala Arg Phe Asn Lys Phe Met Ala Lys Phe Thr Ser Leu Phe
1               5                   10                  15

Gly Arg Arg Gly Val Asp Val Pro Asn Ala Ala His His
            20                  25                  30
```

HORNFLY VACCINE METHODS

CROSS-REFERENCE TO RELATED APPLICATIONS

This application claims priority to and benefit of International Application No. PCT/US18/65407, entitled "Vaccine Compositions and Methods of Making Same," filed Dec. 13, 2018 which claims priority to and benefit of U.S. Provisional Application No. 62/598,658, entitled New Thrombostasins for Horn Fly Vaccine Production, filed Dec. 14, 2017, the contents of which are incorporated in their entirety for all purposes.

BACKGROUND

The horn fly is a major problem affecting cattle in the US and other parts of the world like Latin America. It is estimated that the economic impact on US livestock production is greater than 1 billion per year.

The horn fly produces in its saliva a toxin called Thrombostasin. This toxin, once injected after the bite, interferes with the blood coagulation of cattle causing anemia and allowing the fly to suck blood easily. A Thrombostasin vaccine is one method by which the biological activity of Thrombostasin can be neutralized. When injected into the animal, the vaccine is effective only after an immune response to TS is elicited, and when antibodies produced in response to vaccination protect against disruption of normal clotting function at bite sites.

Vaccine trials performed in cattle in 2004 and 2005 consisted of the TS proteins produced in *E. coli* through recombinant DNA technology. Vaccines were prepared using recombinant TS isoforms TB8 and TS9 (Cupp et al, 2004, Cupp et al, 2005)) and inoculated by intramuscular route of vaccination to elicit an antibody response. Cattle, injected with the vaccine containing the TS isoforms, developed antibodies specific to TS, and decreased blood uptake by horn flies was observed in comparison to cattle vaccinated with ovalbumin. In a follow-up trial reported in 2010, cattle vaccinated with recombinant isoforms TB8 and TS9 again developed antibodies specific to TS, and demonstrated a significant decrease in blood uptake by horn flies during a 20-minute feeding time frame.

While these studies suggest success of a Thrombostasin vaccine, methods of effectively making the vaccine in amounts sufficient to provide the vaccine on a larger scale basis have not been available. Specifically, prior to Applicant's invention, it has not been possible to harvest enough antigen from the fly to produce a commercial vaccine, thus limiting the ability to produce an effective vaccine for the control of the horn fly and its effect on cattle populations. The instant invention seeks to address one or more of the aforementioned needs in the art.

BRIEF SUMMARY

Disclosed herein are fusion proteins comprising a truncated thrombostasin protein having at least 85% sequence homology to a thrombostasin protein, wherein the thrombostasin protein has a carboxy terminal deletion; and a fusion partner protein that is a non-thrombostasin protein. Further disclosed are vaccine compositions thrombostasin proteins having a comprising a carboxy terminal deletion, and methods for inhibiting a response to a thrombostasin protein in a host in need thereof, comprising the disclosed fusion proteins or vaccine compositions. Further disclosed are methods for the preparation of a fusion protein composition.

BRIEF DESCRIPTION OF THE DRAWINGS

This application file contains at least one drawing executed in color. Copies of this patent or patent application publication with color drawing(s) will be provided by the Office upon request and payment of the necessary fee.

Those of skill in the art will understand that the drawings, described below, are for illustrative purposes only. The drawings are not intended to limit the scope of the present teachings in any way.

FIG. 3 depicts the delay in recalcification time induced by horn fly saliva test

DETAILED DESCRIPTION

Definitions

Figure 1:
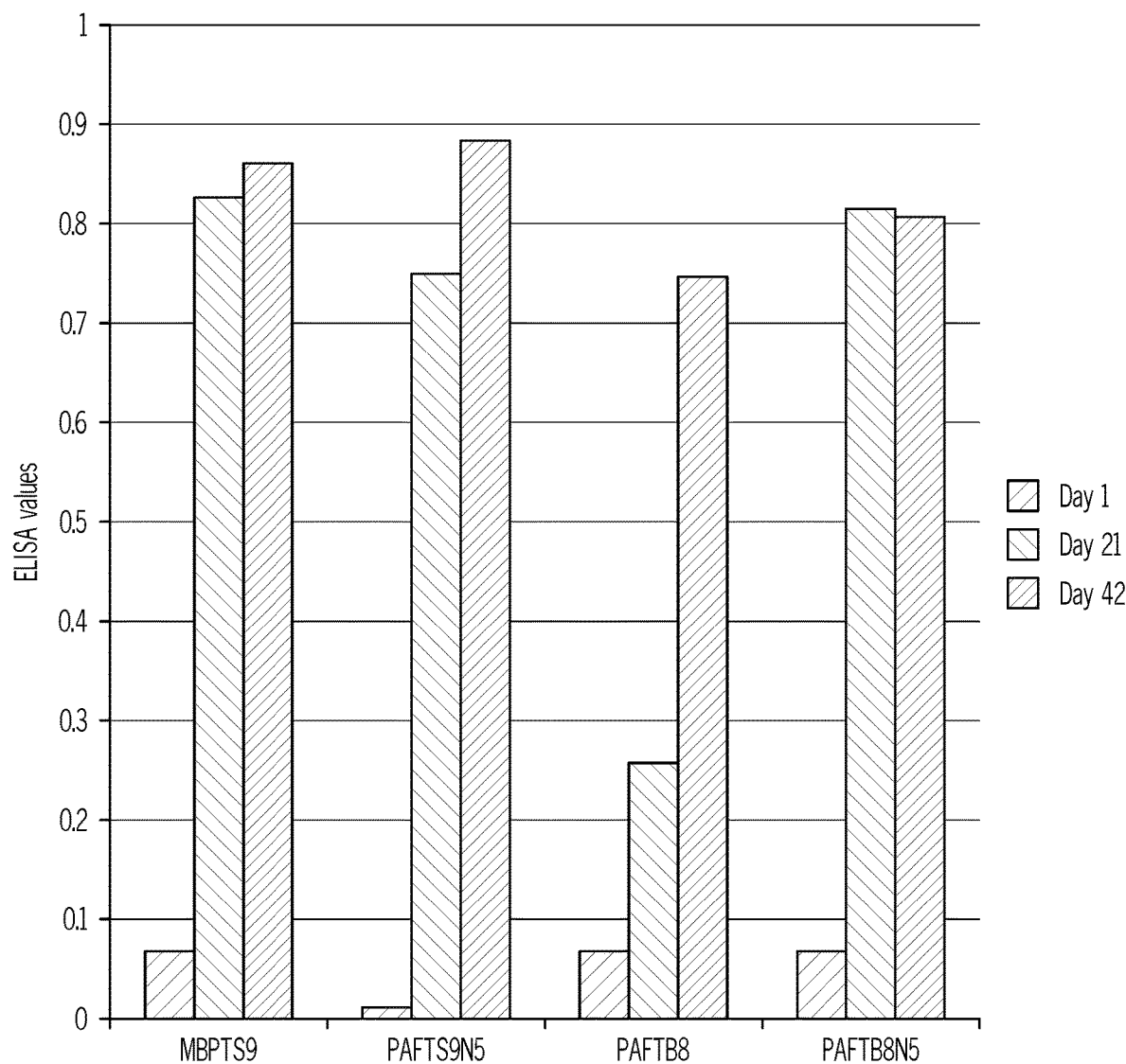
FIG. 1 depicts antibody titers following injection of MBPTS9, PAFTS9NS, PAFTB8 and PAFTB8N5.

Unless otherwise noted, terms are to be understood according to conventional usage by those of ordinary skill in the relevant art. In case of conflict, the present document, including definitions, will control. Preferred methods and materials are described below, although methods and materials similar or equivalent to those described herein may be used in practice or testing of the present invention. All publications, patent applications, patents and other references mentioned herein are incorporated by reference in their entirety. The materials, methods, and examples disclosed herein are illustrative only and not intended to be limiting.

As used herein and in the appended claims, the singular forms "a," "and," and "the" include plural referents unless the context clearly dictates otherwise. Thus, for example, reference to "a method" includes a plurality of such methods and reference to "a dose" includes reference to one or more doses and equivalents thereof known to those skilled in the art, and so forth.

The term "about" or "approximately" means within an acceptable error range for the particular value as determined by one of ordinary skill in the art, which will depend in part on how the value is measured or determined, e.g., the limitations of the measurement system. For example, "about" may mean within 1 or more than 1 standard deviation, per the practice in the art. Alternatively, "about" may mean a range of up to 20%, or up to 10%, or up to 5%, or up to 1% of a given value. Alternatively, particularly with respect to biological systems or processes, the term may mean within an order of magnitude, preferably within 5-fold, and more preferably within 2-fold, of a value. Where particular values are described in the application and claims, unless otherwise stated the term "about" meaning within an acceptable error range for the particular value should be assumed.

As used herein, the term "effective amount" means the amount of one or more active components that is sufficient to show a desired effect. This includes both therapeutic and prophylactic effects. When applied to an individual active ingredient, administered alone, the term refers to that ingredient alone. When applied to a combination, the term refers to combined amounts of the active ingredients that result in the therapeutic effect, whether administered in combination, serially or simultaneously.

"Sequence identity" as used herein indicates a nucleic acid sequence that has the same nucleic acid sequence as a reference sequence, or has a specified percentage of nucleotides that are the same at the corresponding location within a reference sequence when the two sequences are optimally aligned. For example, a nucleic acid or amino acid sequence may have at least 50%, 60%, 70%, 75%, 80%, 85%, 90%, 95%, 96%, 97%, 98%, 99%, or 100% identity to the reference nucleic acid or amino acid sequence. The length of comparison sequences will generally be at least 5 contiguous nucleotides, or at least 10, 11, 12, 13, 14, 15, 16, 17, 18, 19, 20, 21, 22, 23, 24, or 25 contiguous nucleotides, or the full-length nucleotide or amino acid sequence. Sequence identity may be measured using sequence analysis software on the default setting (e.g., Sequence Analysis Software Package of the Genetics Computer Group, University of Wisconsin Biotechnology Center, 1710 University Avenue, Madison, Wis. 53705). Such software may match similar sequences by assigning degrees of homology to various substitutions, deletions, and other modifications.

Prior to Applicant's invention, it has not been possible to harvest enough antigens from the horn fly to produce a commercial vaccine. One possible solution is to clone and express the protein in, for example *E. coli* using a plasmid vector. Despite many attempts, however, Applicant has discovered that it has not been not possible to produce enough antigens using the full-length Thrombostasin genes.

Disclosed herein are fusion proteins that may comprise a truncated thrombostasin protein having at least 85% sequence homology to a thrombostasin protein, wherein the thrombostasin protein comprises a carboxy terminal deletion; and a fusion partner protein that may comprise a non-thrombostasin protein component. By "fusion partner protein" it is meant an amino acid sequence that is fused to the thrombostasin protein and which may be used to improve yield of the fusion protein during the manufacturing process. Generally, and as contemplated herein, the fusion partner protein is contiguous with the thrombostasin protein, in that the fusion partner protein and thrombostasin protein are part of a single sequence. The sequences may, in certain aspects, use additional linker sequence which connect the fusion partner protein and thrombostasin protein.

In one aspect, the fusion partner protein is a non-thrombostasin protein, in that it is does not comprise a sequence having substantial sequence identity to a thrombostasin protein. In one aspect, the truncated thrombostasin protein may be as immunogenic in mammals as a native, non-truncated thrombostasin protein. In other aspects, the immunogenicity may be substantially the same as native, non-truncated thrombostasin protein. In one aspect, the truncated thrombostasin protein produces biologically active antibodies that interfere with the anti-clotting activity of natural thrombostasin from horn fly.

In one aspect, the thrombostasin protein may be selected from TS9 (SEQ ID NO: 1), TS10 (SEQ ID NO: 2), TB8 (SEQ ID NO: 3), TS8 (SEQ ID NO: 4), TS2 (SEQ ID NO: 5), GTS 1 (SEQ ID NO: 6), GTS 2 (SEQ ID NO: 7), GTS 3 (SEQ ID NO: 8), GTS 4 (SEQ ID NO: 9), GTS 5 (SEQ ID NO: 10), GTS 6 (SEQ ID NO: 11), and GTS 7 (SEQ ID NO: 12). In one aspect, the remaining portion of the truncated thrombostasin protein (i.e., the sequence that remains after an N terminal deletion) may be at least 80%, 81%, 82%, 83%, 84%, 85%, 86%, 87%, 88%, 89%, 90%, 91%, 92%, 93%, 94%, 95%, 96%, 97%, 98%, or 99% identical to a sequence selected from any of SEQ ID NOs: 1-12, wherein the thrombostasin protein is capable of being bound by an antibody that specifically binds to a thrombostasin protein selected from SEQ ID NOs: 1-12.

In one aspect, the carboxy terminal deletion may be a deletion of at least 5 amino acids, or at least 6 amino acids, or at least 6 amino acids, or at least 7 amino acids, or at least 8 amino acids, or at least 9 amino acids, or at least 10 amino acids, or at least 11 amino acids, or at least 12 amino acids, or at least 13 amino acids, or at least 14 amino acids, or at least 15 amino acids, or at least 16 amino acids, or at least 17 amino acids, or at least 18 amino acids, or at least 19 amino acids, or at least 20 amino acids, or from about 10 to 35 amino acids, or from about 15 to 30 amino acids, or about 20 to about 25 amino acids, or about 30 amino acids. In one aspect, the truncated thrombostasin protein may be selected from SEQ ID NO: 13, SEQ ID NO: 14, SEQ ID NO: 15, and a combination thereof.

In one aspect, the fusion partner protein may be selected from maltose binding protein (MBP), protein for antigen fusion (PAF), C reactive protein (CRP) or a fragment thereof, β-galactosidase, glutathione-S-transferase, polyhistidine, myelin basic protein (MBP1-9) or a fragment thereof, chicken egg white ovalbumin (OVA) and combinations thereof. Suitable fusion partner proteins for the proteins of the invention are well known to those of skill in the art and include, among others, β-galactosidase, glutathione-S-transferase, poly-histidine and maltose binding protein.

In one aspect, a vaccine composition is disclosed. The vaccine composition may comprise a thrombostasin sequence having a deletion at the C terminal end, wherein said deletion is the last 35 amino acids, the last 34 amino acids, the last 33 amino acids, the last 32 amino acids, the last 31 amino acids, the last 30 amino acids, the last 29 amino acids, the last 28 amino acids, the last 27 amino acids, the last 26 amino acids, the last 25 amino acids, the last 24 amino acids, the last 23 amino acids, the last 22 amino acids, the last 21 amino acids, or the last 20 amino acids. the vaccine composition may further comprising a fusion partner protein.

In one aspect, the vaccine composition may comprise a plurality of fusion proteins comprising a thrombostasin protein, for example, a plurality of fusion proteins including a truncated TS9 protein, a truncated TS10 protein, or one or both of a truncated TB8 protein or truncated TS8 protein. In one aspect, the vaccine composition may comprise a truncated thrombostasin protein and fusion partner protein sequence of SEQ ID NO 16, SEQ ID NO 18, SEQ ID NO 20, SEQ ID NO 21, SEQ ID NO 22, SEQ ID NO 23, or a combination thereof.

In one aspect, the fusion protein of the vaccine composition may be present in an amount sufficient to elicit a biological response in a host. The vaccine composition may further comprising a pharmaceutically acceptable carrier and/or an adjuvant. As used herein, the term "adjuvant" typically refers to a class of substance that can increase the magnitude of the immune response elicited by the fusion protein conjugate beyond that which would be expected, either from the protein alone or from the fusion carrier protein conjugate as described herein in the absence of an adjuvant. In an embodiment, the pharmaceutically acceptable carrier includes an adjuvant. There is no specific limitation on kinds of the adjuvants, examples of which can include but be not limited to aluminum gel adjuvant, oil adjuvant (for example, Freund's complete adjuvant, Freund's incomplete adjuvant and so on) or any combination thereof. Suitable adjuvants will be known to persons skilled in the art. Non-limiting examples of suitable adjuvants include aluminum salts (e.g. aluminum hydroxide, aluminum phosphate and potassium aluminum sulfate (also referred to as Alum)), liposomes, virosomes, water-in-oil or oil-in-water emulsions (e.g. Freund's adjuvant, Montanide®, MF59® and AS03), 3-O-desacyl-4'-monophosphoryl lipid A (MPL) and adjuvants containing MPL (e.g. AS01, AS02 and AS04) and saponin-based adjuvants. Saponin-based adjuvants include saponins or saponin derivatives from, for example, *Quillaja saponaria*, *Panax ginseng* *Panax notoginseng*, *Panax quinquefolium*, *Platycodon grandiflorum*, *Polygala senega*, *Polygala tenuifolia*, *Quillaja brasiliensis*, *Astragalus membranaceus* and *Achyranthes bidentata*. Exemplary saponin-based adjuvants include iscoms, iscom matrix, ISCOMATRIX™ adjuvant, Matrix M™ adjuvant, Matrix C™ adjuvant, Matrix Q™ adjuvant, AbISCO®-100 adjuvant, AbISCO®-300 adjuvant, ISCOPREP™, an ISCOPREP™ derivative, adjuvant containing ISCOPREP™ or an ISCOPREP™ derivative, QS-21, a QS-21 derivative, and an adjuvant containing QS-21 or a QS21 derivative. The vaccine composition as herein described can also be associated with immunomodulatory agents, including, for example, cytokines, chemokines and growth factors. Mixtures of two or more adjuvants within the same vaccine composition are also contemplated herein. Suitable pharmaceutically acceptable carriers (e.g. excipients, diluents, etc.). will be known to persons skilled in the art. For example, a variety of aqueous (pharmaceutically acceptable) carriers may be used, such as buffered water, 0.4% saline, 0.3% glycine, hyaluronic acid and the like. These compositions may be sterilized by conventional, well known sterilization techniques or may be sterile-filtered. The resulting aqueous solutions may be packaged for use as is or lyophilized, the lyophilized preparation being combined with a sterile solution prior to administration. The compositions may further comprise pharmaceutically acceptable auxiliary substances as required to approximate physiological conditions, such as pH-adjusting and buffering agents, tonicity-adjusting agents, wetting agents and the like, for example sodium acetate, sodium lactate, sodium chloride, potassium chloride, calcium chloride, sorbitan monolaurate, triethanolamine oleate, sucrose or other carbohydrates, among many others. Suitable methods for preparing parenterally administrable compounds will be known or apparent to those skilled in the art. The pharmaceutical composition may be in a form suitable for parenteral administration (e.g., subcutaneous, intramuscular or intravenous injection) or in an aerosol form suitable for administration by inhalation, such as by intranasal inhalation or oral inhalation. The pharmaceutical compositions described herein may also be provided in a kit. The kit may comprise additional components to assist in performing the methods as herein described, such as administration device(s), excipients(s), and/or diluent(s). The kits may include containers for housing the various components and instructions for using the kit components in such methods.

The vaccine or pharmaceutical compositions, as described herein, are typically administered in an "effective amount"; that is, an amount effective to elicit any one or more inter alia of a therapeutic or prophylactic effect. Persons skilled in the art would be able, by routine experimentation, to determine an effective, non-toxic amount to include in a pharmaceutical composition or to be administered for the desired outcome. In general, the vaccine and/or pharmaceutical compositions, as disclosed herein, can be administered in a manner compatible with the route of administration and physical characteristics of the recipient and in such a way that it elicits the desired effect(s) (i.e. therapeutically effective, immunogenic and/or protective). For example, the appropriate dosage of a composition may depend on a variety of factors including, but not limited to, a subject's physical characteristics (e.g., age, weight, sex). In some instances, it may be desirable to have several or multiple administrations of the vaccine and/or pharmaceutical compositions, as herein described. For example, the compositions may be administered 1, 2, 3, 4, 5, 6, 7, 8, 9, 10, or more times. The administrations may be from about one day intervals to about twelve-week intervals, and in certain embodiments from about one to about four-week intervals. Periodic re-administration may be required to achieve a desirable therapeutic result, such as a reduction in tumour size and/or a reduction in the occurrence of metastases. It will also be apparent to persons skilled in the art that the optimal course of administration can be ascertained using conventional course of treatment or efficacy or immune status determination tests.

In one aspect, the fusion protein or vaccine composition as disclosed herein may be injected intramuscularly, subcutaneously or any other route of administration.

In one aspect, a method for inhibiting a response to a thrombostasin protein in a host in need thereof is disclosed. In this aspect, the method may comprise the step of administering a therapeutically effective amount of a fusion protein or vaccine composition as described herein to the host. The host may be a mammal, in particular, cattle.

In one aspect, a method for preparation of a thrombostasin deletion mutant fusion protein composition is disclosed. The method may comprise the steps of generating a plasmid for expressing one or more fusion proteins as disclosed herein; causing the plasmid to express the one or more fusion proteins within a host cell; and collecting the one or more fusion proteins from said host cell. In one aspect, the fusion protein may be produced in in *E. coli*. In other aspects, the fusion protein may be produced in any cell production system, such as, for example, bacteria, fungi, insects or mammalian cells. In one aspect, the fusion protein may be produced by chemical peptide synthesis.

Pharmaceutical Compositions

In one aspect, active agents provided herein may be administered in an dosage form selected from intravenous or subcutaneous or intramuscular unit dosage form, oral, parenteral, intravenous, intramuscular, and subcutaneous. In some embodiments, active agents provided herein may be formulated into liquid preparations for, e.g., oral administration. Suitable forms include suspensions, syrups, elixirs, and the like. In some embodiments, unit dosage forms for oral administration include tablets and capsules. Unit dosage forms configured for administration once a day; however, in certain embodiments it may be desirable to configure the unit dosage form for administration twice a day, or more.

In one aspect, pharmaceutical compositions are isotonic with the blood or other body fluid of the recipient. The isotonicity of the compositions may be attained using sodium tartrate, propylene glycol or other inorganic or organic solutes. An example includes sodium chloride. Buffering agents may be employed, such as acetic acid and salts, citric acid and salts, boric acid and salts, and phosphoric acid and salts. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like.

Viscosity of the pharmaceutical compositions may be maintained at the selected level using a pharmaceutically acceptable thickening agent. Methylcellulose is useful because it is readily and economically available and is easy to work with. Other suitable thickening agents include, for example, xanthan gum, carboxymethyl cellulose, hydroxypropyl cellulose, carbomer, and the like. In some embodiments, the concentration of the thickener will depend upon the thickening agent selected. An amount may be used that will achieve the selected viscosity. Viscous compositions are normally prepared from solutions by the addition of such thickening agents.

A pharmaceutically acceptable preservative may be employed to increase the shelf life of the pharmaceutical compositions. Benzyl alcohol may be suitable, although a variety of preservatives including, for example, parabens, thimerosal, chlorobutanol, or benzalkonium chloride may also be employed. A suitable concentration of the preservative is typically from about 0.02% to about 2% based on the total weight of the composition, although larger or smaller amounts may be desirable depending upon the agent selected. Reducing agents, as described above, may be advantageously used to maintain good shelf life of the formulation.

In one aspect, active agents provided herein may be in admixture with a suitable carrier, diluent, or excipient such as sterile water, physiological saline, glucose, or the like, and may contain auxiliary substances such as wetting or emulsifying agents, pH buffering agents, gelling or viscosity enhancing additives, preservatives, flavoring agents, colors, and the like, depending upon the route of administration and the preparation desired. See, e.g., "Remington: The Science and Practice of Pharmacy", Lippincott Williams & Wilkins; 20th edition (Jun. 1, 2003) and "Remington's Pharmaceutical Sciences," Mack Pub. Co.; 18th and 19th editions (December 1985, and June 1990, respectively). Such preparations may include complexing agents, metal ions, polymeric compounds such as polyacetic acid, polyglycolic acid, hydrogels, dextran, and the like, liposomes, microemulsions, micelles, unilamellar or multilamellar vesicles, erythrocyte ghosts or spheroblasts. Suitable lipids for liposomal formulation include, without limitation, monoglycerides, diglycerides, sulfatides, lysolecithin, phospholipids, saponin, bile acids, and the like. The presence of such additional components may influence the physical state, solubility, stability, rate of in vivo release, and rate of in vivo clearance, and are thus chosen according to the intended application, such that the characteristics of the carrier are tailored to the selected route of administration.

For oral administration, the pharmaceutical compositions may be provided as a tablet, aqueous or oil suspension, dispersible powder or granule, emulsion, hard or soft capsule, syrup or elixir. Compositions intended for oral use may be prepared according to any method known in the art for the manufacture of pharmaceutical compositions and may include one or more of the following agents: sweeteners, flavoring agents, coloring agents and preservatives. Aqueous suspensions may contain the active ingredient in admixture with excipients suitable for the manufacture of aqueous suspensions. Lubrimayts, such as stearic acid or magnesium or calcium salts thereof, polytetrafluoroethylene, liquid paraffin, vegetable oils and waxes, sodium lauryl sulfate, magnesium lauryl sulfate, polyethylene glycol, starch, talc, pyrogenic silica, hydrated silicoaluminate, and the like, may be included in tablet formulations. Surfactants may also be employed, for example, anionic detergents such as sodium lauryl sulfate, dioctyl sodium sulfosuccinate and dioctyl sodium sulfonate, cationic such as benzalkonium chloride or benzethonium chloride, or nonionic detergents such as polyoxyethylene hydrogenated castor oil, glycerol monostearate, polysorbates, sucrose fatty acid ester, methyl cellulose, or carboxymethyl cellulose. Controlled release formulations may be employed wherein the active agent or analog(s) thereof is incorporated into an inert matrix that permits release by either diffusion or leaching mechanisms. Slowly degenerating matrices may also be incorporated into the formulation. Other delivery systems may include timed release, delayed release, or sustained release delivery systems. Coatings may be used, for example, nonenteric materials such as methyl cellulose, ethyl cellulose, hydroxyethyl cellulose, methylhydroxy-ethyl cellulose, hydroxypropyl cellulose, hydroxypropyl-methyl cellulose, sodium carboxymethyl cellulose, providone and the polyethylene glycols, or enteric materials such as phthalic acid esters. Dyestuffs or pigments may be added for identification or to characterize different combinations of active agent doses. When administered orally in liquid form, a liquid carrier such as water, petroleum, oils of animal or plant origin such as peanut oil, mineral oil, soybean oil, or sesame oil, or synthetic oils may be added to the active ingredient(s). Physiological saline solution, dextrose, or other saccharide solution, or glycols such as ethylene glycol, propylene glycol, or polyethylene glycol are also suitable liquid carriers. The pharmaceutical compositions may also be in the form of oil-in-water emulsions. The oily phase may be a vegetable oil, such as olive or arachis oil, a mineral oil such as liquid paraffin, or a mixture thereof. Suitable emulsifying agents include naturally-occurring gums such as gum acacia and gum tragamayth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsions may also contain sweetening and flavoring agents.

Pulmonary delivery of the active agent may also be employed. The active agent may be delivered to the lungs while inhaling and traverses across the lung epithelial lining to the blood stream. A wide range of mechanical devices designed for pulmonary delivery of therapeutic products may be employed, including but not limited to nebulizers, metered dose inhalers, and powder inhalers, all of which are familiar to those skilled in the art. These devices employ formulations suitable for the dispensing of active agent. Typically, each formulation is specific to the type of device employed and may involve the use of an appropriate propellant material, in addition to diluents, adjuvants, and/or carriers useful in therapy. In some embodiments, an active agent provided herein may be administered by intravenous, parenteral, or other injection, in the form of a pyrogen-free, parenterally acceptable aqueous solution or oleaginous suspension. Suspensions may be formulated according to methods well known in the art using suitable dispersing or wetting agents and suspending agents. The preparation of acceptable aqueous solutions with suitable pH, isotonicity, stability, and the like, is within the skill in the art. In some embodiments, a pharmaceutical composition for injection may include an isotonic vehicle such as 1,3-butanediol, water, isotonic sodium chloride solution, Ringer's solution, dextrose solution, dextrose and sodium chloride solution, lactated Ringer's solution, or other vehicles as are known in the art. In addition, sterile fixed oils may be employed conventionally as a solvent or suspending medium. For this purpose, any bland fixed oil may be employed including synthetic mono or diglycerides. In addition, fatty acids such as oleic acid may likewise be used in the formation of injectable preparations. The pharmaceutical compositions may also contain stabilizers, preservatives, buffers, antioxidants, or other additives known to those of skill in the art.

The duration of the injection may be adjusted depending upon various factors, and may comprise a single injection administered over the course of a few seconds or less, to 0.5, 0.1, 0.25, 0.5, 0.75, 1, 2, 3, 4, 5, 6, 7, 8, 9, 10, 11, 12, 13, 14, 15, 16, 17, 18, 19, 20, 21, 22, 23, or 24 hours or more of continuous intravenous administration.

In some embodiments, active agents provided herein may additionally employ adjunct components conventionally found in pharmaceutical compositions in their art-established fashion and at their art-established levels. Thus, for example, the compositions may contain additional compatible pharmaceutically active materials for combination therapy, such as insecticides or insect growth regulators and the like, anti-anemic drugs such as iron dextran, ferrous sulfate, EPO, deferoxamine, folic acid, and vitamin B12, or may contain materials useful in physically formulating various dosage forms, such as excipients, dyes, thickening agents, stabilizers, preservatives or antioxidants.

In some embodiments, the active agents provided herein may be provided to an administering physician or other health care professional in the form of a kit. The kit is a package which houses a container which contains the active agent(s) in a suitable pharmaceutical composition, and instructions for administering the pharmaceutical composition to a subject. The kit may optionally also contain one or more additional therapeutic agents currently employed for treating one or more disease states as described herein. For example, a kit containing one or more compositions comprising active agents provided herein in combination with one or more additional active agents may be provided, or separate pharmaceutical compositions containing an active agent as provided herein and additional therapeutic agents may be provided. The kit may also contain separate doses of a active agent provided herein for serial or sequential administration. The kit may optionally contain one or more diagnostic tools and instructions for use. The kit may contain suitable delivery devices, e.g., syringes, and the like, along with instructions for administering the active agent(s) and any other therapeutic agent. The kit may optionally contain instructions for storage, reconstitution (if applicable), and administration of any or all therapeutic agents included. The kits may include a plurality of containers reflecting the number of administrations to be given to a subject.

EXAMPLES

The following non-limiting examples are provided to further illustrate embodiments of the invention disclosed herein. It should be appreciated by those of skill in the art that the techniques disclosed in the examples that follow represent approaches that have been found to function well in the practice of the invention, and thus may be considered to constitute examples of modes for its practice. However, those of skill in the art should, in light of the present disclosure, appreciate that many changes may be made in the specific embodiments that are disclosed and still obtain a like or similar result without departing from the spirit and scope of the invention.

Example 1

The following yield were obtained with the following systems in flasks or fermenters:

| CLONE | YIELD |
| --- | --- |
| BL-21 Escherichia coli, pVEXK-H6-TS9 | 0 |
| Escherichia coli, Rosetta TS9 | 10 µg/ml |
| BL-21 Escherichia coli, pVEXKB-Ntag-TB8 | 0 |
| BL-21 Escherichia coli, pVEXK-TS9-CtagH8 | 0 |

In typical recombinant protein production, the recombinant protein will represent 15-30% of the total protein present. Fermentations of the Rosetta TS9 strain a yielded TS9 concentrations anywhere from 0.1 to 0.4% of the total protein. Scaling up this construct or another similar TS9 or TB8 construct, would require a significant increase in the production fermentation titer in order to make it an economically viable process. Accordingly, new discoveries have been needed in order to overcome this major technical hurdle for producing recombinant Thrombostasin protein.

Data collected by Applicant has further elucidated the toxic effects of Thrombostasin on biological systems. During procedures to clone and express the isoforms of Thrombostasin in highly regulated expression systems for large scale production of recombinant proteins, depending on the expression system, it has been found that all four isoforms of Thrombostasin (TB8, TSB, TS9, or TS10) when cloned into various host/plasmid expression systems cause cell death, lysis, or aberrant growth.

In order to overcome this problem, fusion protein genes were added to the TS genes into an E. coli expression vector. Two fusion proteins provided similar results summarized in the Table below for two isoforms of Thrombostasin TS9 and TB8. As the yields were still not high enough for commercial use, a small deletion was made at the C terminal portion of the Thrombostasin gene. In one aspect, the deletion may be about 30 amino acids (in one aspect, the deletion may be LRARFNKFMA KFTSLFGRRR GVDVPNAAHH (SEQ ID NO 24) for TS9). Surprisingly, this deletion boosted the production of the protein in tissue culture flasks and fermenter. Exemplary fusion proteins include MBP and PAF. MBP stands for maltose binding protein and is well known in the art, see, for example, di Guan, C; Li, P; Riggs, P D; Inouye, H (1988). "Vectors that facilitate the expression and purification of foreign peptides in Escherichia coli by fusion to maltose-binding protein". Gene. 67 (1): 21-30. PAF (Proteins for Antigen Fusion) is an example of another fusion protein that may be used with the instant disclosure.

| TS Antigen | Method of Production | Yield in Flask | Yield in Fermenter |
| --- | --- | --- | --- |
| TS9 | TS9 | Very poor | |
| | PAF TS9 | 10 mg/ml | 70 mg/ml |
| | PAF TS9N5 | 40 mg/ml | 100 mg/ml |
| | MBPTS9 | 10 mg/ml | |
| TB8 | TB8 | No expression | |
| | PAFTB8 | 10 mg/ml | |
| | PAFTB8N5 | 25 mg/ml | |

Exemplary amino acid sequences of the newly created proteins are as follows. It should be understood by one of ordinary skill in the art that a suitable composition may include some variation while still maintaining function, for example, including the disclosed sequences of about 85%, 86%, 87%, 88%, 89%, 90%, 91%, 92%, 93%, 94%, 95%, 96%, 97%, 98%, 99%, or any range of the foregoing.

MBPTS9: Protein length=556 MW=61501.0. The MBP sequence is indicated in bold. The PAF sequence is indicated in bold/italics. Regular text represents the thrombostasin protein.

(SEQ ID NO 16)
MKIEEGKLVI WINGDKGYNG LAEVGKKFEK DTGIKVTVEH

PDKLEEKFPQ VAATGDGPDI IFWAHDRFGG YAQSGLLAEI

TPDKAFQDKL YPFTWDAVRY NGKLIAYPIA VEALSLIYNK

DLLPNPPKTW EEIPALDKEL KAKGKSALMF NLQEPYFTWP

LIAADGGYAF KYENGKYDIK DVGVDNAGAK AGLTFLVDLI

KNKHMNADTD YSIAEAAFNK GETAMTINGP WAWSNIDTSK

VNYGVTVLPT FKGQPSKPFV GVLSAGINAA SPNKELAKEF

LENYLLTDEG LEAVNKDKPL GAVALKSYEE ELAKDPRIAA

TMENAQKGEI MPNIPQMSAF WYAVRTAVIN AASGRQTVDE

ALKDAQTNSS SNNNNNNNNN NLGIEGRISE FGS QNVLSGR

RQHGAQGLSG YSGDNDWGYY GEAGAPGSDY SGSSGQWAPL

DFDYNSLPGL SGYNHEQQDY EEDSYRHVRS AGPITLQLDD

DDDDDSGIPI FEMDDEDEDS NDNQKFPLSF ERFPENEKNQ

EGLRARFNKF MAKFTSLFGR RRGVDVPNAA HHHHHH

PAFTS9 Protein length = 304 Molecular weight 34101.2.
(SEQ ID NO 17)
*MKLTIESTPF NVAEGKEVLL LVHNLPQHLF GYSWYKGERV*

*DGNRQIIGYV IGTQQATPGP AYSGREIIYP NASLLIQNII*

*QNDTGFYTLH VIKSDLVNEE ATGQFRVYPE LPKPSISSNN*

*SKPVEDKDAV AFTCEPETQD A* QNLVSGRRQ HGAQGLSGYS

GDNDWGYYGE AGAPGSDYSG SSGQWAPLDF DYNSLPGLSG

YNHEQQDYEE DSYRHVRSAG PITLQLDDDD DDDSGIPIFE

MDDEDEDSND NQKFPLSFER FPENEKNQEG LRARFNKFMA

KFTSLFGRRR GVDVPNAAHH HHHH

PAFTS9N5 Protein length = 276 MW = 30892.0.
(SEQ ID NO 18)
*MKLTIESTPF NVAEGKEVLL LVHNLPQHLF GYSWYKGERV*

*DGNRQIIGYV IGTQQATPGP AYSGREIIYP NASLLIQNII*

*QNDTGFYTLH VIKSDLVNEE ATGQFRVYPE LPKPSISSNN*

*SKPVEDKDAV AFTCEPETQD A* QNLVSGRRQ HGAQGLSGYS

GDNDWGYYGE AGAPGSDYSG SSGQWAPLDF DYNSLPGLSG

YNHEQQDYEE DSYRHVRSAG PITLQLDDDD DDDSGIPIFE

MDDEDEDSND NQKFPLSFER FPENEKNQEG HHHHHH

PAFTB8 Protein length = 304 MW = 34040.2.
(SEQ ID NO 19)
*MKLTIESTPF NVAEGKEVLL LVHNLPQHLF GYSWYKGERV*

*DGNRQIIGYV IGTQQATPGP AYSGREIIYP NASLLIQNII*

*QNDTGFYTLH VIKSDLVNEE ATGQFRVYPE LPKPSISSNN*

*SKPVEDKDAV AFTCEPETQD A* QNLVSGRRQ HGAQGLSGYS

GDNDWGYYGE AGAPGSDYSG SSGQWAPLDF DYNSLPGLSG

YNHEQQDYEE DSYRHVRSAG PITLQLDDDD DDDSGIPIFE

MDDEDVDSND NQKFPLSFER FPENEKNQVG LRARFNKFMA

KFTSLFGRRR GVNVPNAAHH HHHH

PAFTB8N5 Protein length = 276 MW = 30833.0.
(SEQ ID NO 20)
*MKLTIESTPF NVAEGKEVLL LVHNLPQHLF GYSWYKGERV*

*DGNRQIIGYV IGTQQATPGP AYSGREIIYP NASLLIQNII*

*QNDTGFYTLH VIKSDLVNEE ATGQFRVYPE LPKPSISSNN*

*SKPVEDKDAV AFTCEPETQD A* QNLVSGRRQ HGAQGLSGYS

GDNDWGYYGE AGAPGSDYSG SSGQWAPLDF DYNSLPGLSG

YNHEQQDYEE DSYRHVRSAG PITLQLDDDD DDDSGIPIFE

MDDEDVDSND NQKFPLSFER FPENEKNQVG HHHHHH

A similar process can be applied to all isoforms of Thrombostasin, for example:

MBPTS9N5 Protein length = 528 MW = 58292.8.
(SEQ ID NO 21)
MKIEEGKLVI WINGDKGYNG LAEVGKKFEK DTGIKVTVEH

PDKLEEKFPQ VAATGDGPDI IFWAHDRFGG YAQSGLLAEI

TPDKAFQDKL YPFTWDAVRY NGKLIAYPIA VEALSLIYNK

DLLPNPPKTW EEIPALDKEL KAKGKSALMF NLQEPYFTWP

LIAADGGYAF KYENGKYDIK DVGVDNAGAK AGLTFLVDLI

KNKHMNADTD YSIAEAAFNK GETAMTINGP WAWSNIDTSK

VNYGVTVLPT FKGQPSKPFV GVLSAGINAA SPNKELAKEF

LENYLLTDEG LEAVNKDKPL GAVALKSYEE ELAKDPRIAA

TMENAQKGEI MPNIPQMSAF WYAVRTAVIN AASGRQTVDE

ALKDAQTNSS SNNNNNNNNN NLGIEGRISE FGS QNVLSGR

RQHGAQGLSG YSGDNDWGYY GEAGAPGSDY SGSSGQWAPL

DFDYNSLPGL SGYNHEQQDY EEDSYRHVRS AGPITLQLDD

DDDDDSGIPI FEMDDEDEDS NDNQKFPLSF ERFPENEKNQ

EGHHHHHH

MBPTS10N5 Protein length = 528 MW = 58262.8.
(SEQ ID NO 22)
MKIEEGKLVI WINGDKGYNG LAEVGKKFEK DTGIKVTVEH

PDKLEEKFPQ VAATGDGPDI IFWAHDRFGG YAQSGLLAEI

TPDKAFQDKL YPFTWDAVRY NGKLIAYPIA VEALSLIYNK

DLLPNPPKTW EEIPALDKEL KAKGKSALMF NLQEPYFTWP

LIAADGGYAF KYENGKYDIK DVGVDNAGAK AGLTFLVDLI

KNKHMNADTD YSIAEAAFNK GETAMTINGP WAWSNIDTSK

VNYGVTVLPT FKGQPSKPFV GVLSAGINAA SPNKELAKEF

LENYLLTDEG LEAVNKDKPL GAVALKSYEE ELAKDPRIAA

TMENAQKGEI MPNIPQMSAF WYAVRTAVIN AASGRQTVDE

```
ALKDAQTNSS SNNNNNNNNN NLGIEGRISE FGS QNVLSGR

RQHGAQGLSG YSGDNDWGYY GEAGAPGSDY SGSSGQWAPL

DFDYNSLPGL SGYNHEQQDY EEDSYRHVRS AGPITLQLDD

DDDDDSGIPI FEMDDEDEDS NDNQKFPLSF ERFPENEKNQ

VGHHHHHH

MBPTB8N5 Protein length = 528 MW = 58232.8.
                                         (SEQ ID NO 23)
MKIEEGKLVI WINGDKGYNG LAEVGKKFEK DTGIKVTVEH

PDKLEEKFPQ VAATGDGPDI IFWAHDRFGG YAQSGLLAEI

TPDKAFQDKL YPFTWDAVRY NGKLIAYPIA VEALSLIYNK

DLLPNPPKTW EEIPALDKEL KAKGKSALMF NLQEPYFTWP

LIAADGGYAF KYENGKYDIK DVGVDNAGAK AGLTFLVDLI

KNKHMNADTD YSIAEAAFNK GETAMTINGP WAWSNIDTSK

VNYGVTVLPT FKGQPSKPFV GVLSAGINAA SPNKELAKEF

LENYLLTDEG LEAVNKDKPL GAVALKSYEE ELAKDPRIAA

TMENAQKGEI MPNIPQMSAF WYAVRTAVIN AASGRQTVDE

ALKDAQTNSS SNNNNNNNNN NLGIEGRISE FGS QNLVSGR

RQHGAQGLSG YSGDNDWGYY GEAGAPGSDY SGSSGQWAPL

DFDYNSLPGL SGYNHEQQDY EEDSYRHVRS AGPITLQLDD

DDDDDSGIPI FEMDDEDVDS NDNQKFPLSF ERFPENEKNQ

VGHHHHHH
```

MPBTS8N5 has the same composition than MBPTS9N5, the difference between TS9 and TS8 is removed with the deletion.

MBPTS9, PAFTS9NS, PAFTB8 and PAFTB8N5 were mixed with a commercial adjuvant ENABL (Vaxliant Laboratories) and injected into 12 rabbits twice on Day 1 and 21. Blood samples were collected on Day 1, 21 and 42, the sera separated and the antibody titers determined by ELISA. The results are shown in FIG. 1. Other adjuvants known in the art may be used, including, for example, Al hydroxide and freund's adjuvant. In FIG. 1, the first bar indicates day 1, the second bar indicates day 21, the third bar indicates day 42. All antigens tested were very immunogenic, generating antibodies to Thrombostasin after only one injection. Surprisingly, the gene deletion did not affect the antibody production.

Figure 2:
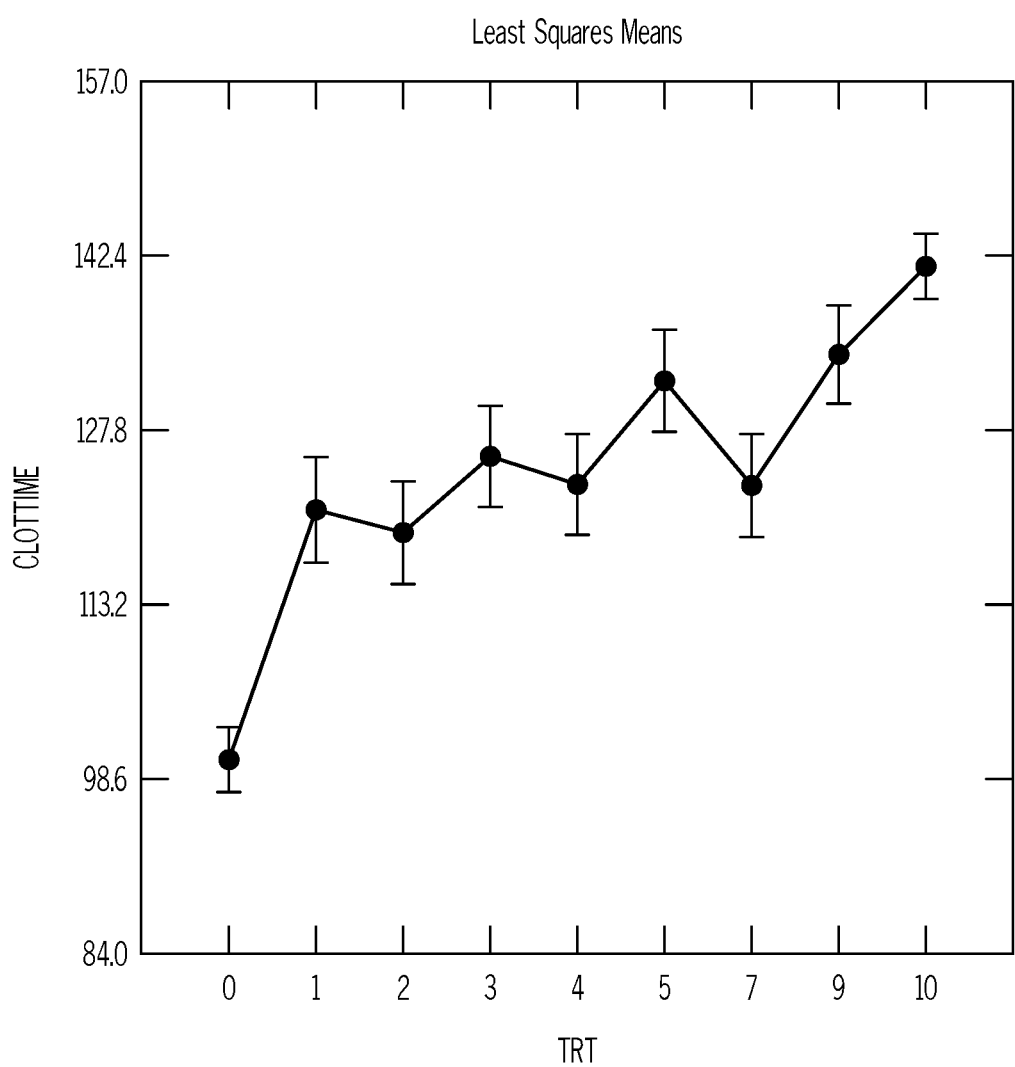
FIG. 2 depicts the ability of antibodies to inhibit the anticoagulant activity of Thrombostasin contained in the salivary glands of horn fly.

Finally, the antibodies were tested for the ability to inhibit the anticoagulant activity of Thrombostasin contained in the salivary glands of horn flies using the delay in recalcification time induced by horn fly saliva test (RCT). Briefly sample or control buffer, diluted in 50 mM Tris, pH 7.4 at 37° C., 0.15 M NaCl, 0.1% bovine serum albumin (BSA) and 0.1% polyethylene glycol) 8000 (PEG 8000) (TSBP buffer) were added to reference normal plasma (Accuclot, Sigma Chemical Company, St. Louis, Mo.); the mixture was incubated at 37° C. for 3 min before adding $CaCl_2$ solution (10 mM final concentration). The time between the addition of $CaCl_2$ and the first sign of the mass formation (clot) was recorded as clotting time. The results are summarized in FIG. 2, wherein Treatment 0: negative control, normal coagulation; Treatment 1: vaccinated with MBPTS9+saliva; Treatment 2: vaccinated with PAFTS9N5+saliva; Treatment 5: vaccinated with PAF TB8+saliva; Treatment 9: unvaccinated+saliva; Treatment 10: positive control saliva only. All vaccines inhibited the action of horn fly saliva. Treatment 2 (the truncated TS9N5 antigen) had the greatest effect. The unvaccinated group was not different from the positive control. Gene deletion of Thrombostasin at the C terminal end of the genes overcame the cell toxicity and increased the production of the proteins to commercially acceptable levels without changing the immunogenicity or the antigens or the biological activity of the antibodies generated by those antigens.

Example 2

PURPOSE—The purpose of this experiment is to evaluate the ability of an experimental vaccine using truncated thrombostasin antigens to generate antibody in cattle in cattle. The vaccine, composed 3 recombinant truncated TS antigens with adjuvant, will be injected intramuscularly into test animals. The antibody produce will be evaluated for their ability to neutralize the anti-coagulant activity of the saliva of horn flies.

VACCINE—The saliva of the horn fly, Haematobia irritans irritans contains thrombostasin proteins that prevent clotting of the blood of the bitten host, allowing the fly to continue to draw blood. The vaccine described in this example contains 3 recombinant proteins identified as MBPpTS9N5 (SEQ ID NO: 21), MBPpTS10N5 (SEQ ID NO:22) and MBPpTB8 N5 (SEQ ID NO: 23). MBP is a fusion protein used to enhance the immunogenicity of the vaccine, and TS9, TS10 and TB8 are isotypes of the thrombostasin proteins commonly found the saliva of horn flies in the USA. The vaccine stimulates the immune system to produce antibodies that mitigate the anti-clotting effects of the saliva of the horn fly.

Vaccine Administration

Route of exposure—Intramuscular injection of recombinant proteins suspended in a saline buffer with an added licensed adjuvant ENABL from VaxLiant.

Dose levels—100 μg of each of the above-mentioned protein mixed in an adjuvant.

Dose schedule—3 groups: group A vaccinated on day 0, group B vaccinated on day 0 and day 21, group C acting as control.

Calves

Species & breed—Bos torus and probably Angus or Angus crossbreeds

Sex—castrated males or intact females

Source—Local calf ranch

Age/weight—4-6 months old, 300-500 lbs

Number—11

Husbandry and Animal Care

Acclimation period—3-4 weeks

Housing—Corral

Environment—Opened and closed

Diet & water—Routine by New Mexico State University

Veterinary care—As provided by New Mexico State University

EXPERIMENTAL DESIGN—11 calves are used in this experiment and randomized into two groups of four and one control group of three. An experimental vaccine consisting of 3 recombinant truncated thrombostasins with adjuvant is administered by intramuscular injection in the following treatments:

1. Single dose of the vaccine, day 0
2. Priming dose of vaccine, day 0 and booster on day 21
3. Control; 1 ml sterile saline, days 0 and 21

Blood is drawn on days 0, 21 and 35. Serum is be separated into 5 volumes of ½ cc and frozen. Antibody titers to the vaccine antigens is determined on sera collected on each day the blood is drawn. Serum titers of antibodies to the vaccine antigens is determined by an ELISA test.

VACCINE DESCRIPTION AND PREPARATION—Purified recombinant antigen(s) and adjuvants are suspended in an appropriate saline suspending agent.

Post Vaccination Animal Care

General health—Calves will be observed daily for adverse events related to vaccination and overall health.

Blood collection—Blood is collected from the jugular vein using a vacutainer tube and a 16-gauge needle while the animal is constrained in a squeeze chute. Serum is separated and processed for further use in antibody testing.

Analysis of Blood

Blood profile—Blood is drawn into red stoppered vacutainer tubes which allow for separation of cellular and fluid components of the blood.

Serum preservation—The separated serum is divided into small volumes (½ cc) in separate containers and frozen at −75 degrees F.

Antibody titer determination—Antibodies against the antigens in the vaccine are titered using an ELISA test. The antigens used in the test are the three truncated antigens and four full length thrombostasin protein TS5, TSB, TS9 and TS10.

Delay in recalcification time induced by horn fly saliva test (RCT): Briefly, sample or control buffer, diluted in 50 mM Tris, pH 7.4 at 37 C, 0.1 NaCl, 0.1% bovine serum albumin (BSA) and 0.1% polyethylene glycol 8000 (PEG 8000) (TSBP buffer) are added to reference normal plasma (Acculot Sigma Chemical Company, St Louis Mo.). The mixture is incubated at 37° C. for 3 minutes before adding $CaCl_2$ solution (10 mM final concentration. The time between the addition of $CaCl_2$ and the first sign of the mass formation (clot) was recorded as clotting time).

The results are shown in FIG. 3 and the Table below. The data show a number of positive effects: 1. The truncated proteins are antigenic, successfully producing antibodies in cattle despite the modifications. 2. A booster effect is observed after a primary and then a booster vaccination. 3. The truncated antigens appear to produce antibodies that react with the full-length antigens, indicating that antibodies to the full length or the truncated antigens will react with the particular isotype of thrombostasin in the saliva; the antibodies inhibit the biological effect of the thrombostasin and different antigens can be used in combination without interfering with antibody production. Applicant further found that the ELISA antibody titers are such that commercialization of the vaccine is possible. In one aspect, two vaccinations may be used—a primary and a booster vaccination.

Inhibition of the Anticoagulant Effect

| Calf # | Trt. | Clot Time | Saliva | Inh. Saliva |
| --- | --- | --- | --- | --- |
| 758 | A | 109.2 | 142.6 | −33.4 |
| 763 | A | 105.7 | 135.3 | −29.6 |
| 768 | A | 113.5 | 135.3 | −21.8 |
| 767 | A | 127 | 142.6 | −15.6 |
| Mean = | | 113.85 | 138.95 | −25.1 |
| 765 | B | 100.5 | 135.3 | −34.8 |
| 760 | B | 130.9 | 142.6 | −11.7 |
| 762 | B | 121.3 | 135.3 | −14 |
| 766 | B | 125.6 | 142.6 | −17 |
| Mean = | | 119.575 | 138.95 | −19.375 |
| 759 | C | 123.5 | 142.6 | −19.1 |
| 761 | C | 122.41 | 135.3 | −12.89 |
| 764 | C | 138 | 135.3 | 2.7 |
| Mean = | | 127.97 | 137.7333 | 9.76333333 |

Examining the data, it is clear that serum samples from vaccinated cattle were more effective in disrupting TS in horn fly saliva than were serum samples from the controls. Surprisingly, the serum from cattle vaccinated only once seem to be more effective the those from cattle vaccinated twice but the difference was not statistically significant (analysis of variance analysis p=0.186).

REFERENCES

MS Cupp et al. Evaluation of a recombinant salivary gland protein (thrombostasin) as a vaccine candidate to disrupt blood-feeding by horn flies. Vaccine 22: 2285-2297 (2004).

MS Cupp et al. Vaccination of cattle with recombinant salivary proteins of horn flies (Haematobiairritansirritans). Proc of World Assoc for Adv of Vet Parasit (WAAVP) Abstract 94 (2005).

MS Cupp et al Salivary gland thrombostasin isoforms differentially regulate blood uptake of horn flies on control and thrombostasin-vaccinated cattle. J. Med. Entomol. 47: 610-617 (2010).

All percentages and ratios are calculated by weight unless otherwise indicated.

All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "20 mm" is intended to mean "about 20 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications may be made without departing from the spirit and scope of the invention. It is therefore intended to cover in the appended claims all such changes and modifications that are within the scope of this invention.

What is claimed is:

1. A method for inhibiting a response to a thrombostasin protein in a host in need thereof, comprising administering a therapeutically effective amount of a composition comprising one or more truncated thrombostasin proteins, said one or more truncated thrombostasin proteins having a sequence selected from SEQ ID NO: 20, SEQ ID NO: 21, SEQ ID NO: 22, SEQ ID NO: 23, and combinations thereof.

2. The method of claim 1, wherein said administration is selected from one or both of intramuscular injection and subcutaneous injection.

3. The method of claim 1, wherein said composition comprises a truncated thrombostasin protein comprising SEQ ID NO: 21, a truncated thrombostasin protein comprising SEQ ID NO: 22, and a truncated thrombostasin protein comprising SEQ ID NO: 23.

4. The method of claim 3, wherein said host is a cow.

5. The method of claim 3, wherein said host is a calf.

6. The method of claim 3, wherein said host is selected from Bos torus, Angus, or an Angus crossbreed.

7. The method of claim 1, wherein said composition comprises a pharmaceutically acceptable carrier.

8. The method of claim 1, wherein said composition comprises an adjuvant.

9. The method of claim 1, wherein said composition is administered in intervals of from about one day to about 12 weeks.

10. The method of claim 1, wherein said composition is administered a first dose at day 0 and a second dose at day 21.

11. The method of claim 1, wherein said administration results in antibodies in said host that mitigate an anti-clotting effect of hornfly saliva in said host.

12. The method of claim 1, wherein said composition is administered in an amount sufficient to elicit a biological response in said host.

* * * * *